United States Patent [19]

Buckler

[11] 4,100,352
[45] Jul. 11, 1978

[54] CYCLOHEXANONE-5,6-BENZO ANALOGUES OF PROSTAGLANDIN

[75] Inventor: Robert Thomas Buckler, Edwardsburg, Mich.

[73] Assignee: Miles Laboratories, Inc., Elkhart, Ind.

[21] Appl. No.: 789,131

[22] Filed: Apr. 20, 1977

Related U.S. Application Data

[62] Division of Ser. No. 671,423, Mar. 29, 1976.

[51] Int. Cl.² .................. C07C 177/00; C07C 69/76
[52] U.S. Cl. .................................. 560/53; 560/55;
260/456 P; 260/465 F; 260/515 R; 260/520 R;
424/308; 424/317
[58] Field of Search ................ 560/53; 260/520 R

[56] References Cited

FOREIGN PATENT DOCUMENTS 845,179  2/1977  Belgium .................... 560/53

OTHER PUBLICATIONS

Derwent Abstr. 08596x/05, NL 7508-301, 14-01-76.
Derwent Abstr. 01790x/01, U.S. 3928-418, 23-12-75.
Derwent Abstr. 66750t-b, DT2209990-Q, 21-09-72.

*Primary Examiner*—Paul J. Killos
*Attorney, Agent, or Firm*—Myron B. Sokolowski

[57] ABSTRACT

Disclosed are prostaglandin analogues having the structural formula,

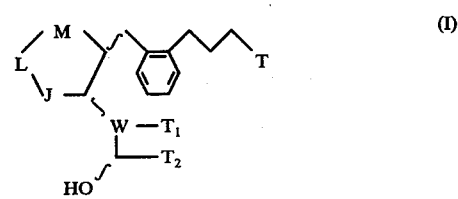

in which:

T is selected from the group consisting of carboxyl, alkoxycarbonyl or cyano;

M is selected from the group consisting of carbonyl, R-hydroxymethylene or S-hydroxymethylene;

L is selected from the group consisting of methylene or methine, provided L is methine only if J is methine;

J is selected from the group consisting of methylene, ethylene, R-hydroxymethylene, S-hydroxymethylene or methine, provided J is methine only if L is methine;

W is selected from the group consisting of

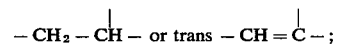

$T_1$ and $T_2$ are attached to adjacent carbon atoms;

$T_1$ is selected from the group consisting of hydrogen or phenyl, provided $T_1$ is phenyl only if $T_2$ is lower alkyl;

$T_2$ is selected from the group consisting of n-pentyl or lower alkyl, provided $T_2$ is lower alkyl only if $T_1$ is phenyl;

or $T_1$ and $T_2$ are joined together to form an alkylene group of 4 or 6 carbon atoms. Also disclosed are methods for preparing such prostaglandin analogues.

5 Claims, No Drawings

CYCLOHEXANONE-5,6-BENZO ANALOGUES OF PROSTAGLANDIN

This is a division, of application Ser. No. 671,423, filed Mar. 29, 1976.

BACKGROUND OF THE INVENTION

1. Field of the Invention

Compounds of this invention are analogues of natural prostaglandins.

Natural prostaglandins are twenty-carbon atom alicyclic compounds related to prostanoic acid which has the following structure:

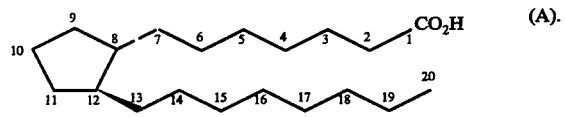

By convention, the carbon atoms of A are numbered sequentially from the carboxylic carbon atom. An important stereo-chemical feature of A is the trans-orientation of the side-chains $C_1$–$C_7$ and $C_{13}$–$C_{20}$. All natural prostaglandins have this orientation. In A, as elsewhere in this specification, a dashed line (---) indicates projection of a covalent bond below the plane of a reference carbon atom or ring (alpha-configuration), while a wedged line (—) represents direction above that plane (beta-configuration). Those conventions apply to all compounds subsequently discussed in this specification.

In one system of nomenclature suggested by N. A. Nelson [(J. Med. Chem., 17: 911 (1972)], prostaglandins are named as derivatives or modifications of the natural prostaglandins. In a second system, the I.U.P.A.C. (International Union of Pure and Applied Chemistry) system of nomenclature, prostaglandins are named as substituted heptanoic acids. Yet a third system of nomenclature is frequently used by those skilled in the prostaglandin art. In this third system (also described by Nelson), all prostaglandins are named as derivatives or modifications of prostanoic acid (structure A) or prostane (the hydrocarbon equivalent of structure A). This system is used by Chemical Abstracts and may become an I.U.P.A.C. accepted system.

Natural prostaglandins have the structures,

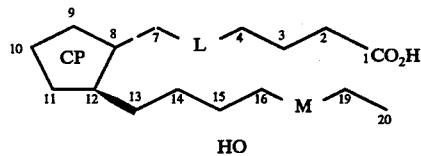

in which: L and M may be ethylene or cis-vinylene radicals and the five-membered ring 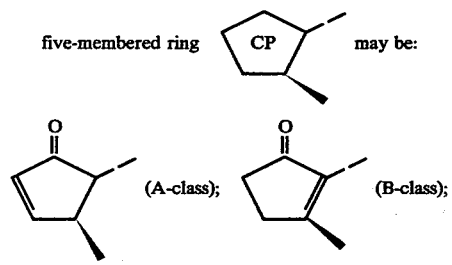 may be:

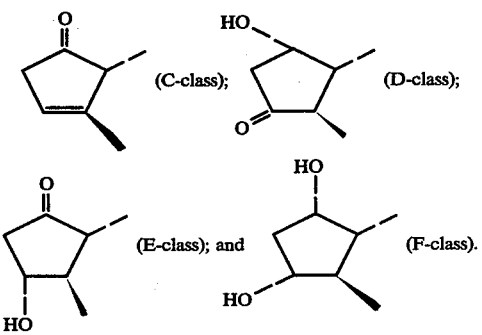

Prostaglandins are classified according to the functional groups present in the five-membered ring and the presence of double bonds in the ring or chains. Prostaglandins of the A-class (PGA or prostaglandin A) are characterized by an oxo group at $C_9$ and a double bond at $C_{10}$–$C_{11}$ ($\Delta^{10,11}$); those of the B-class (PGB) have an oxo group at $C_9$ and a double bond at $C_8$–$C_{12}$ ($\Delta^{11,12}$); compounds of the C-class (PGC) contain an oxo group at $C_9$ and a double bond at $C_{11}$–$C_{12}$ ($\Delta^{11,12}$); members of the D-class (PGD) have an oxo group at $C_{11}$ and an alpha-oriented hydroxy group at $C_9$; prostaglandins of the E-class (PGE) have an oxo group at $C_9$ and an alpha-oriented hydroxyl group at $C_{11}$; and members of the F-class (PGF) have an alpha-directed hydroxyl group at $C_9$ and an alpha-oriented hydroxyl group at $C_{11}$. Within each of the A, B, C, D, E, and F classes of prostaglandins are three subclassifications based upon the presence of double bonds in the side-chains at $C_5$–$C_6$, $C_{13}$–$C_{14}$, or $C_{17}$–$C_{18}$. The presence of a trans-unsaturated bond only at $C_{13}$–$C_{14}$ is indicated by the subscript numeral 1; thus, for example, $PGE_1$ (or prostaglandin $E_1$) denotes a prostaglandin of the E-type (oxo group at $C_9$ and an alpha-hydroxyl at $C_{11}$) with a trans-double bond at $C_{13}$–$C_{14}$. The presence of both a trans-double bond at $C_{13}$–$C_{14}$ and a cis-double bond at $C_5$–$C_6$ is denoted by the subscript numeral 2; for example, $PGE_2$. Lastly, a trans-double bond at $C_{13}$–$C_{14}$, a cis-double bond at $C_5$–$C_6$ and a cis-double bond at $C_{17}$–$C_{18}$ is indicated by the subscript numeral 3; for example, $PGE_3$. The above notations apply to prostaglandins of the A, B, C, D, and F series as well, however, in the latter the alpha-orientation of the hydroxyl group at $C_9$ is indicated by the subscript Greek letter $\alpha$ after the numerical subscript.

The three systems of nomenclature as they apply to natural $PGF_{3\alpha}$ are shown below:

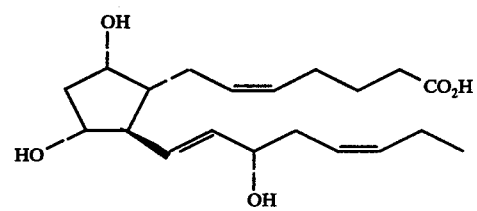

Nelson System:
Prostaglandin $F_{3\alpha}$ or $PGF_{3\alpha}$ (shortened form) I.U.P.A.C. System:
7-[3R, 5S-Dihydroxy-2R-(3S-hydroxy-1E, 5Z-octadienyl)-cyclopent-1R-yl]-5Z-heptenoic acid Third System (Chemical Abstracts):

(5Z, 9α, 11α, 13E, 15S, 17Z)-9,11,15-trihydroxy-prosta-5,13,17-trien-1-oic acid.

It is important to note that in all natural known prostaglandins there is an alpha-oriented hydroxyl group at $C_{15}$. In the Cahn-Ingold-Prelog system of defining stereochemistry, that $C_{15}$ hydroxyl group is in the S-configuration. The Cahn-Ingold-Prelog system is used to define stereochemistry of any asymmetric center outside of the carbocyclic ring in all three systems of nomenclature described above. This is in contrast to some prostaglandin literature in which the α, β designations are used, even at $C_{15}$.

11-Deoxy derivatives of PGE and PGF molecules have not yet been found to occur as such in nature, but constitute a class of compounds which possess biological activity related to the parent compounds. Formula β represents 11-deoxy PGE and PGF compounds when:

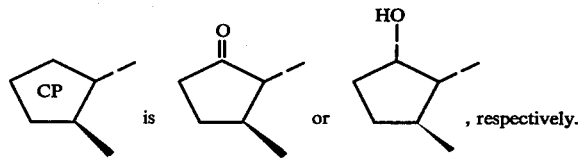

In this formula, and others of this patent specification a swuug dash or serpentine line (∼) denotes a covalent bond which can be either in the alpha configuration (projecting below the plane of a reference carbon atom or ring) or in the beta configuration (projecting above the plane of a reference carbon atom or ring).

$PGF_{62}$ molecules also do not occur as such in nature, but constitute a class of compounds which possess biological activity related to the parent compounds. Formula β represents $PGF_{62}$ compounds when:

9-Deoxy derivatives of PGE do not occur as such in nature, but constitute a class of compounds which possess biological activity related to the parent compounds. Formula β represents 9-deoxy PGE compounds when:

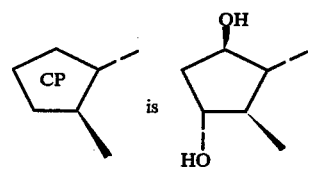

9-Deoxy-$\Delta^{9,10}$ derivatives of PGE have not been found to occur as such in nature, but constitute a class of compounds which possess biological activity related to the parent compounds. Formula β represents 9-deoxy-$\Delta^{9,10}$ PGE compounds when:

9a-homo- and 9a-homo-11-deoxy-molecules have not been found to occur as such in nature, but constitute a class of compounds which possess biological activity related to the parent compounds. Formula B represents 9α-homo- and 9α-homo-11-deoxy-compounds of PGE and PGF when: -epi-5,6

11a-Homo- derivatives of PGE, PGF and PGA molecules do not occur as such in nature, but constitute classes of compounds which are expected to possess biological activity related to the parent compounds. Formula B represents 11a-homo- derivatives of PGE, PGF and PGA molecules when:

11-Epi-PGE and PGF molecules do not occur as such in nature, but constitute classes of compounds which possess biological activity related to the parent compounds. Formula B represents 11-epi-compounds of PGE and PGF when:

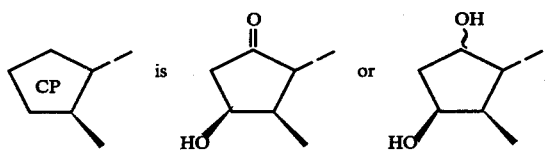

8Iso-, 12iso or 8,12-bis iso (ent) prostaglandins do not occur as such in nature, but constitute classes of compounds which possess biological activity related to the parent compounds. Formula B represents 8iso-, 12iso or 8, 12-bis iso (ent) compounds when:

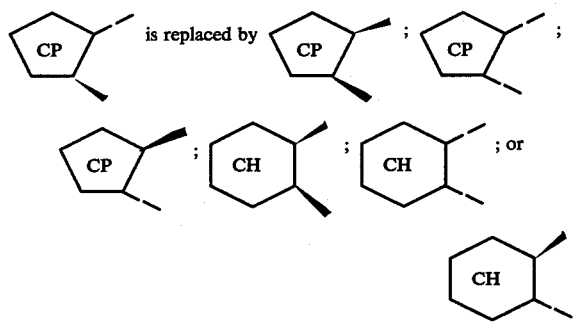

These iso modifications of Formula B may be divided into all of the sub-classes with varying ring oxygenation as described above.

Recent research indicates that prostaglandins are ubiquitous in animal tissues and that prostaglandins, as well as their synthetic analogues, have important biochemical and physiological effects in mammalian endocrine, reproductive, central and peripheral nervous, sensory, gastro-intestinal, hematic, respiratory, cardiovascular, and renal systems.

In mammalian endocrine systems, experimental evidence indicates prostgalandins are involved in the control of hormone synthesis or release in hormone-secretory glands. In rats, for example, $PGE_1$ and $PGE_2$ increase release of growth hormone while $PGA_1$ increased synthesis of that hormone. In sheep, $PGE_1$ and $PGF_{1\alpha}$ inhibit ovarian progesterone secretion. In a variety of mammals, $PGF_{1\alpha}$ and $PGF_{2\alpha}$ act as luteolytic factors. In mice, $PGE_1$, $PGE_2$, $PGF_{1\alpha}$ and $PGF_{1\beta}$ increase thyroid activity. In hypophysectimized rats, $PGE_1$, $PGE_2$ and $PGF_{1\alpha}$ stimulate steriodogenesis in the adrenal glands.

In the mammalian male reproductive system, $PGE_1$ contracts the smooth muscle of the vas deferens. In the female reproductive system, PGE and $PGF_{60}$ compounds contract uterine smooth muscle. In general, PGE, PGB and PGA compounds relax in vitro human uterine muscle strips, while those of the $PGF_\alpha$ class contract such isolated preparations. PGE compounds in general promote fertility in the female reproductive system while $PGF_{2\alpha}$ has contragestational effects. $PGF_{2\alpha}$ also appears to be involved in the mechanism of menstruation. In general, $PGE_2$ exerts potent oxytocic effects in inducing labor, while $PGF_{2\alpha}$ induces spontaneous abortions in early pregnancy.

$PGF_\alpha$ and PGE compounds hve been isolated from a variety of nervous tissue and they seem to act as neurotransmitters. $PGE_1$ retards whereas $PGF_{2\alpha}$ facilitates transmission in motor pathways in the central nervous system. It has been reported that $PGE_1$ and $PGE_2$ inhibit transmitter release from adrenergic nervie endings in the guinea pig.

Prostaglandins stimulate contraction of gastrointestinal smooth muscle in vivo and in vitro. In dogs, $PGA_1$, $PGE_1$ and $PGE_2$ inhibit gastric secretion. $PGA_1$ exhibits similar activity in man.

In most mammalian respiratory tracts, compounds of the PGE and PGF class relax in vitro preparations of tracheal smooth muscle. In that preparation, $PGE_1$ and $PGE_2$ relax while $PGF_{2\alpha}$ contracts the smooth muscle. PGE and PGF compounds are normally found in the human lung, and it is postulated that some cases of bronchial asthma involve an imbalance in the production or metabolism of those compounds.

Prostaglandins are involved in certan hematic mechanisms in mammals. $PGE_1$, for example, inhibits thromobogenesis in vitro through its effects on blood platelets.

In a variety of mammalian cardiovascular systems, compounds of the PGE and PGA class are vasodilators whereas those of the $PGF_\alpha$ class are vasoconstrictors, by virtue of their action on vascular smooth muscle.

Prostaglandins are naturally found in the kidney and reverse experimental and clinical renoprival hypertension. The clinical implications of prostaglandins and their analogues are far-ranging and include, but are not limited to the following: in obstetrics and gynecology, they may be useful in fertility control, treatment of menstrual disordes, induction of labor, and correction of hormone disorders; in gastroenterology, they may be useful in the treatment of peptic ulcers and various disorders involving motility, secretion, and absorption in the gastrointestinal tract; in the respiratory areas, they may be beneficial in therapy of brochial asthma and other diseases involving bronchoconstriction; in hematology, they may have utility as anti-clotting agents in diseses such as venous thrombosis, thrombotic coronary occlusion and other diseases involving thrombi; in circulatory diseases they have therapeutic utility in hypertension, peripheral vasopathies, and cardiac disorders.

SUMMARY

The present invention relates to prostaglandin analogues having the structural formula,

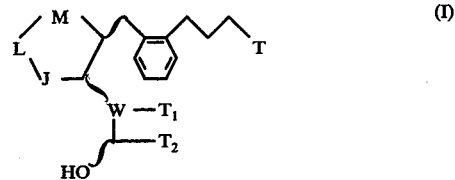

(I)

in which:

T is selected from the group consisting of caboxyl, alkoxycarbonyl or cyano;

M is selected from the group consisting of carbonyl, R-hydroxymethylene or S-hydroxymethylene;

L is selected from the group consisting of methylene or methine, provided L is methine only if J is methine;

J is selected from the group consisting of methylene, ethylene, R-hydroxymethylene, S-hydroxymethylene or methine, provided J is methine only if L is methine;

W is selected from the group consisting of

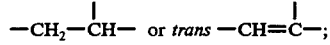

$T_1$ and $T_2$ are attached to adjacent carbon atoms;

$T_1$ is selected from the group consisting of hydrogen or phenyl, provided $T_1$ is phenyl only if $T_2$ is lower alkyl;

$T_2$ is selected from the group consisting of n-pentyl or lower alkyl, provided $T_2$ is lower alkyl only if $T_1$ is phenyl;

or $T_1$ and $T_2$ are joined together to form an alkylene group of 4 or 6 carbon atoms.

As employed with reference to the compounds of the invention, the term, "alkoxycarbonyl" (at times referred to as "COOAlk") shall means and include groups of the formula

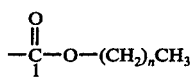

wherein $n$ is from 0 to 2 inclusive. Note that, following conventionally established numerical designation for natural prostaglandins, where T is a carboxy, cyano or carbinol group, the carbon atom in such group is the first-numbered. Where T is an alkoxycarbonyl group, the carbon atom of the oxo radical is designated the first (i.e., numbered "1") carbon atom of the structure.

As employed herein, "lower alkyl" (at times referred to as "1-alk") shall mean and include aliphatic groups having from 1 to 3 carbon atoms.

Note that the condition, "$T_1$ and $T_2$ are attached to adjacent carbon atoms" specifies that $T_1$ is invariably attached on the carbon atom corresponding to "$C_{14}$" of the parent compounds whether W is

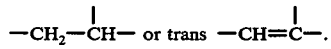

A structural feature common to all of the compounds of the invention is the replacement of the $C_5$–$C_6$ portion of the natural prostaglandins and/or derivatives thereof by an o-phenylene group.

Comprehended by the present invention are certain preferred 11-deoxy compounds wherein, if L and J are both methylene, then: either T is alkoxycarbonyl or, preferably, cyano; or W is

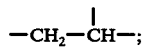

or $T_1$ is phenyl; or $T_1$ and $T_2$ are joined together to form an alkylene group of 4 or 6 carbon atoms.

Comprehended by the presented invention are preferred compounds of subgeneric structures representing analogues of the A-, E-, and F-series or clases of the prostaglandins and/or derivatives thereof. Theus when M is carbonyl, compounds of the invention have a formula generally characteristic of both the A- and E- classes of prostaglandins:

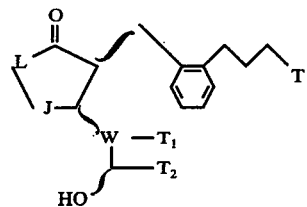

Where M is carbonyl, L is methylene or methine and J is R-hydroxymethylene, S-hydroxymethylene or ethylene, compounds of the invention are analogues of the A- and/or E-classes of prostaglandins and may include the 11 deoxy and/or 9a-homo derivatives thereof. More particularly, where M is carbonyl, L is methylene and J is ethylene compounds of the invention are 11 deoxy-9a-homo- analogues of the E-class having the formula:

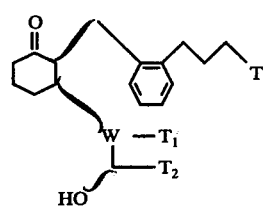

Where M is carbonyl, L is methylene, and J is methylene, compounds of the invention are 11-deoxy analogues of the E-class having the formula:

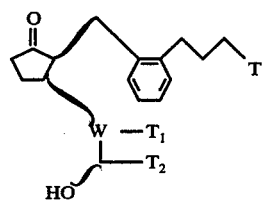

Where M is carbonyl, L is methylene and J is R-hydroxymethylene or S-hydroxymethylene, compounds of the invention are E-class analogues having the formula:

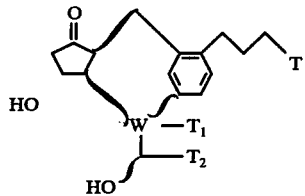

Where M is carbonyl, L is methine and J is methine, compounds of the invention are A-class analogues having the formula:

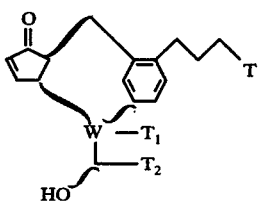

Where, however, M is R-hydroxymethylene or S-hydroxymethylene, L is methylene and J is R-hydroxymethylene or S-hydroxymethylene, compounds of the invention are F-class analogues having the formula:

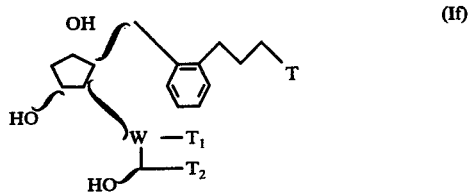

(If)

Preparation of the compound of the present invention and having the structure Ib, Ic, Id, Ie, If, generally proceeds by the 1,4-conjugate addition of organocopper reagents to certain ketones as reported by Sih, et al. [J. Amer. Chem. Soc. 97:857, 865 (1975) and references cited therin]. Specifically, compounds having the stucture Ib are prepared in the manner outlined in Table A from certain ketons IV (themselves prepared from the diones II, the synthesis of which is outlined in Table D) and certain lithium cuprates V (prepared in the manner outlined in Table E). Preparation of certain halovinyl alcohols XXII necessary for preparation of some cuprates useful in the practice of the invention is outlined in Table F. Preparation of compounds having the structure Ic from the ketones IX (again, prepared from the diones II) is outlined in Table B. Preparation of compounds of the invention having the structures Id, Ie and If from certain ketones XVI (the preparation of which is outlined in Table G) is outlined in Table C.

TABLE A
SYNTHETIC PATHWAY FOR PREPARATION OF COMPOUNDS OF STRUCTURE Ib

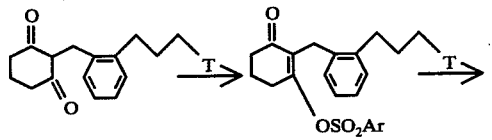

II   III

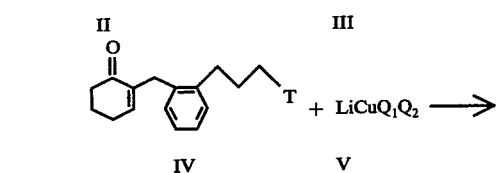

IV   V a... T = CN
b... T = COOAlk
c... T = COOH $Q_2 =$ 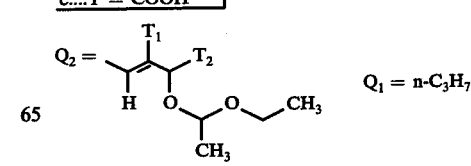 (partial) $Q_1 = n\text{-}C_3H_7$

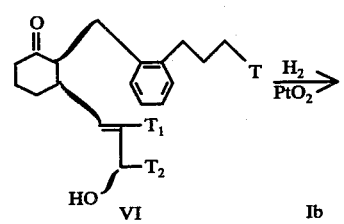

VI   Ib

TABLE A-continued
SYNTHETIC PATHWAY FOR PREPARATION OF COMPOUNDS OF STRUCTURE Ib

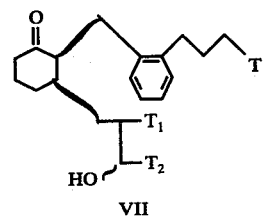

VII

TABLE B
SYNTHETIC PATHWAY FOR PREPARATION OF COMPOUNDS OF STRUCTURE Ic

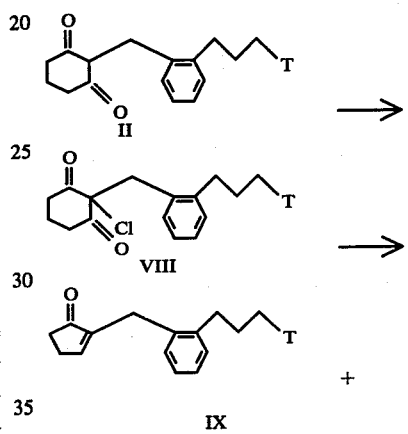

II

VIII

IX

LiCuQ₁Q₂ ⟶

V

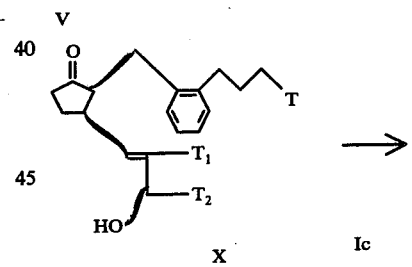

X   Ic

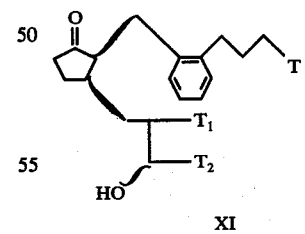

XI a.... T = CN
b.... T = COOAlk
c.... T = COOH $Q_2 =$ 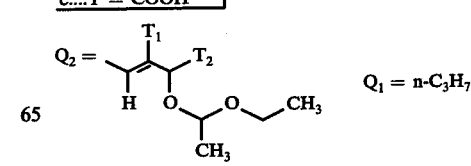

$Q_1 = n\text{-}C_3H_7$

TABLE C
SYNTHETIC PATHWAY FOR PREPARATION OF COMPOUNDS OF STRUCTURES Id, Ie, AND If

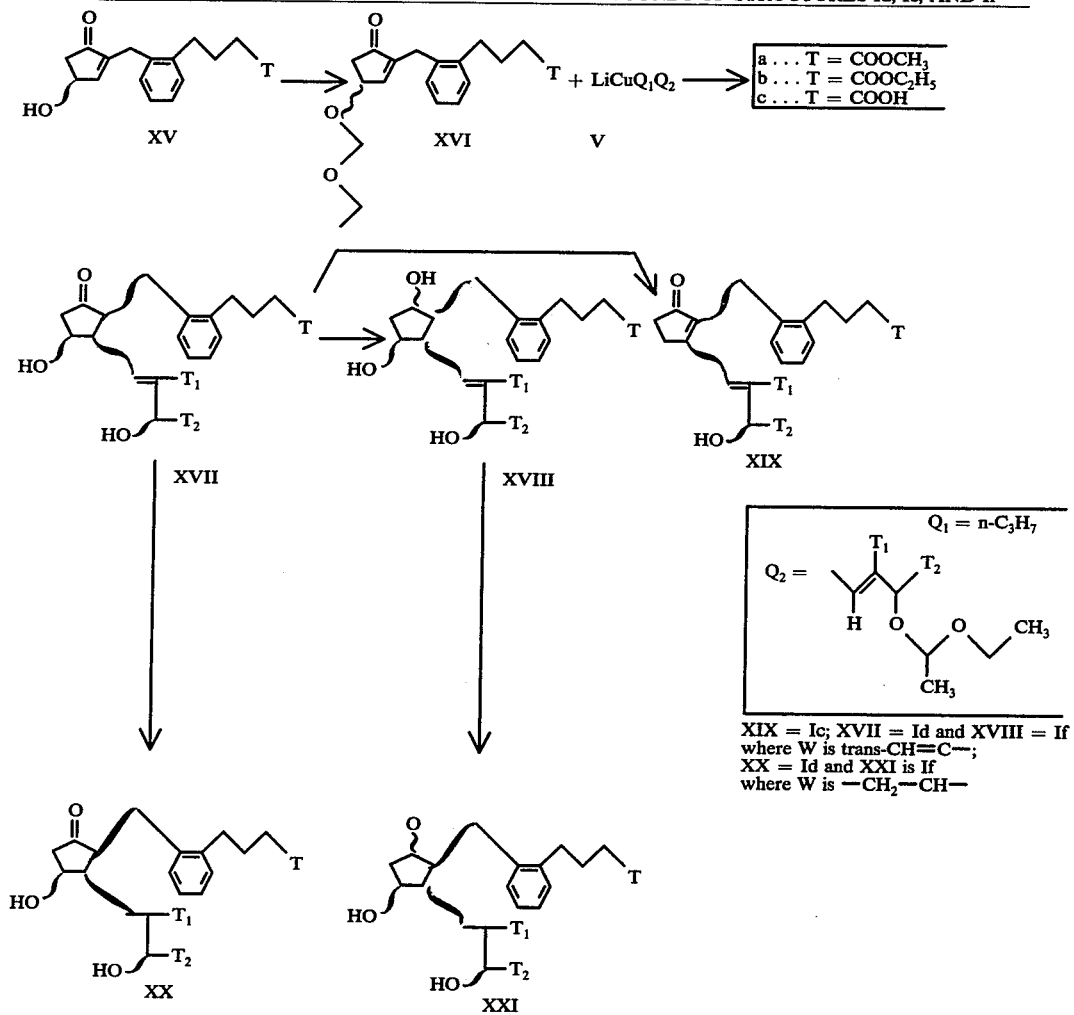

In Table A, a selected 2-substituted benzyl-1,3-cyclohexanedione II (see, Table D) is converted to the enol sulfonate III (Ar 32 mesityl) with 2-mesitylepesulfonyl chloride. These sulfonates are not usually isolated but are reduced directly with sodium borohydride to give, after hydrolysis, the unsaturated ketone IV. These unsaturated ketones are reacted with selected lithium cuprates V [see, House, et al., Org. Chem. 38:3893 (1973); Corey, et al., J. Amer. Chem. Soc. 94:7210 (1972); and Tables E and F] to give, after hydrolysis, the compounds Ib either as the 11-deoxy-9-a-homo-$E_1$ series analogue VI (wherein W is trans —CH=C—) or, upon hydrogenation, the 13,14-dihydro-11-deoxy-9-a-homo-$E_1$ series analogue VII (wherein W is —CH$_2$—CH—).

In Table B, a selected dione II is converted to the chlorodione VIII which can be rearranged to the unsaturated ketones IX [Buchi, et al., J. Org. Chem. 36:2021 (1971)]. The reaction of these with lithium cuprate complexes V produces, after after hydrolysis, the compounds Ic either as the 11-deoxy-$E_1$ series analogue X or, upon hydrogenation, the dihydro-11-deoxy-$E_1$ series analogue XI.

In Table C, a selected ketone XV (see Table G), upon protection of the hydroxy function as in XVI, is reacted with lithium cuprate to form, upon hydrolysis, the compounds Id either as the $E_1$-series analogue XVII or, upon hydrogenation, the dihydro-$E_1$ series anlaogue XX. Reduction of the ketone function in XVII leads to compounds of If, either as $F_1$-series analogue XVIII or, upon hydrogenation, the dihydro-$F_1$-series analgoue XXI. The dehydration of compounds XVII to give compounds Ie, is represented by XIX.

TABLE D
SYNTHETIC PATHWAY FOR PREPARATION OF CERTAIN DIONES FOR USE IN PREPARING COMPOUNDS OF STRUCTURES Ib AND Ic
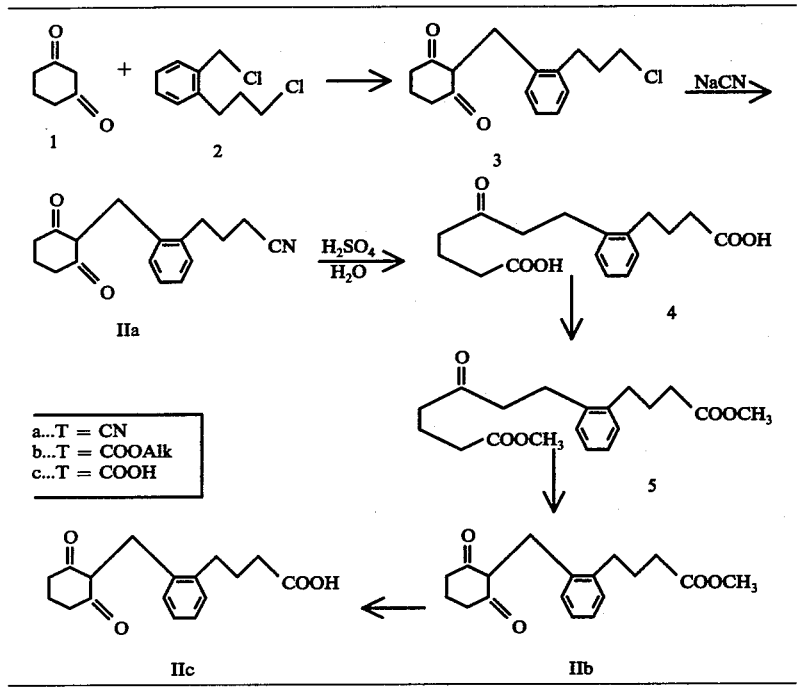
TABLE E
SYNTHETIC PATHWAY FOR PREPARATION OF CERTAIN LITHIUM CUPRATES
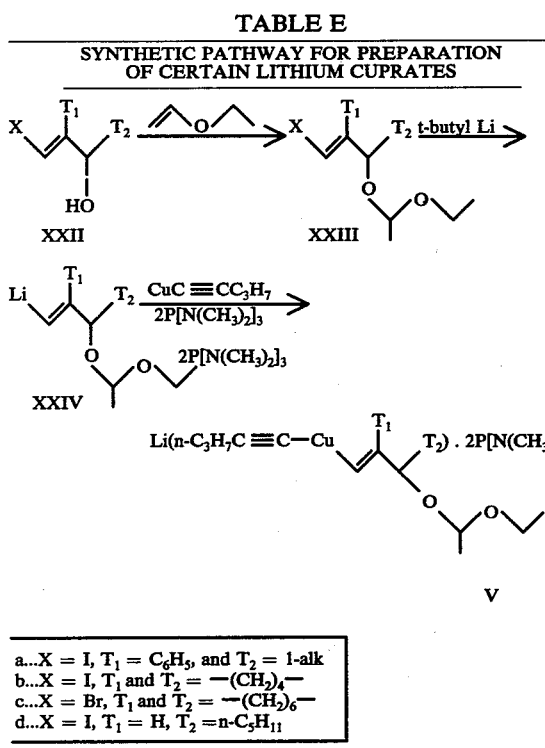
TABLE F
SYNTHETIC PATHWAY FOR PREPARATION OF CERTAIN IODOVINYL ALCOHOLS
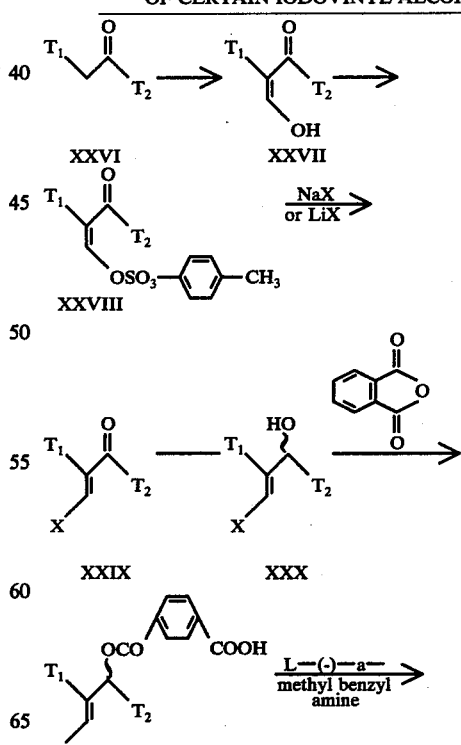

TABLE F-continued
SYNTHETIC PATHWAY FOR PREPARATION OF CERTAIN IODOVINYL ALCOHOLS

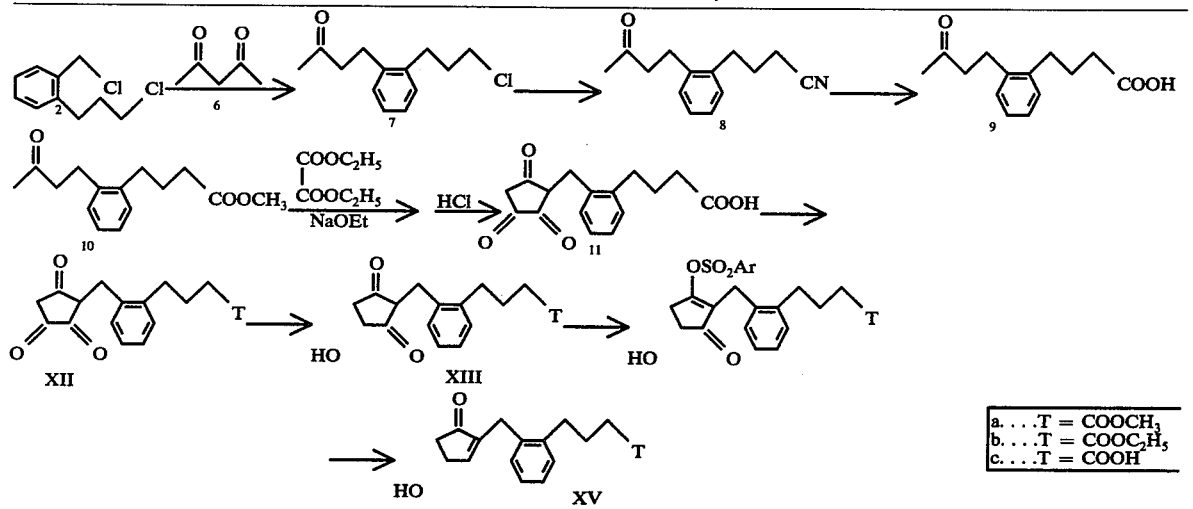

a...X = I, $T_1$ = $C_6H_5$, and $T_2$ = 1-alk
b...X = I, $T_1$ and $T_2$ = —$(CH_2)_4$—
c...X = Br, $T_1$ and $T_2$ = —$(CH_2)_6$—
d...X = I, $T_1$ = H, $T_2$ = n-$C_5H_{11}$ to phthalate esters XXXI. These acids are reacted with L-(-)-a-methyl benzylamine to give the diastereomeric amine salts [Kluge, et al., J. Amer. Chem. Soc. 94:7827 (1972)].

Several recrystallizations gives the resolved salts which regenerate the optically pure alcohols XXII on hydrolysis with concentrated sodium hydroxide. Both the β-halovinyl alcohols XXII and the ketones XV possess free hydroxyl groups that must be protected during the reaction with the lithium cuprate reagents V by converting them to the ethyl vinyl ether adducts XXIII and XVI before use.

TABLE G
SYNTHETIC PATHWAY FOR PREPARATION OF CERTAIN KETONES FOR USE IN PREPARING COMPOUNDS OF STRUCTURES Id, Ie AND If a....T = $COOCH_3$
b....T = $COOC_2H_5$
c....T = COOH

Table D illustrates preparation of the diones II for use in the preparations of Tables A and B. Compound 1 1,3-cyclohexanedione is alkylated with 2-(3-chloropropyl)benzyl chloride 2 [Page, et al., J. Amer. Chem. Soc. 75:2053 (1953)] to give the dione 3. The displacement of the chloro group by cyanide ion gives the cyanodione IIa. The latter may be carried on through the synthesis of Table A or hydrolyzed with minearl acid to the keto diacid 4 which may be converted to the diester 5. Subsequently the diester 5 can be cyclized to produce the dione ester IIb which in turn can be converted to the acid IIc.

Table E illustrates formation of lithium cuprates V through reaction of resolved iodovinyl alcohols XXII with ethylvinyl ether to give mixed acetals XXIII which, in turn react with t-butyl lithium to yield the lithio derivative XXIV. Treatment of XXIV with copper n-propylacetylide complexed with hexamethylphosphorous triamide gives the lithium cuprate reagent.

Table F illustrates preparation of certain halovinyl alcohols XXII wherein the appropriate ketone XXVI is treated with ethyl formate under basic conditions to give formyl ketones XXVII. These react with p-toluenesulfonyl chloride in the presence of tertiary amines to produce the enol tosylates XXVIII. When reacted with sodium or potassium halides, the enol tosylates give the β-halovinyl ketones XXIX which are not usually purified but reduced directly with sodium borohydride to racemic alcohols XXX. The optical resolution of the alcohols is accomplished by converting them Table G illustrates preparation of certain ketones for use in the synthesis of Table C beginning with alkylation of 2,4-pentane dione 6 with 2 to yield the chloroketone 7 [Boatman, et al., J. Org. Chem. 30:3321 (1965)]. Treatment of the latter with cyanide ion gives the cyano ketone 8 which is hydrolyzed to the keto acid 9 and esterified to the keto ester 10. Condensation of 10 with two equivalents of diethyl oxalate under basic conditions [Katsube, et al., Agr. Biol. Chem. 33:1078 (1969)] gives, after hydrolysis, the trione acid 11. Esterification of 11 with methanol or ethanol gives the esters XII. Reduction of 11 leads to the hydroxydione XIII. Treatment of XIII with 2-mesitylene sulfonyl chloride gives the enol sulfonate XIV which is not isolated but reduced to the unsaturated ketone XV.

Briefly stated, the following are among the methods of the present invention.

1. Forming an 11-deoxy-9-a-homo-$E_1$ series prostaglandin analogue of Formula Ib by: (a) preparing a selected 2-substituted benzyl-1,3-cyclohexane dione II; (b) forming the unsaturated ketone IV from II via the enol sulfonate III; and (c) reacting the ketone IV with a selected lithium cuprate V to form the desired product VI which may be hydrogenated to the 13,14-dihydroform VII.

2. Forming an 11-deoxy-9-a-homo-$E_1$ prostaglandin analogue of Formula Ic by: (a) converting the dione II to the chlorodione VIII; (b) rearranging the chlorodione VIII to the unsaturated ketone IX; and (c) reacting the ketone IX with a selected lithium cuprate V to form the desired product X which may be hydrogenated to the dihydro form XI.

3. Forming an $E_1$-prostaglandin analogue of Formula Id by: (a) preparing an unsaturated ketone XV from the intermediates XII, XIII and XIV prepared from 2-(3-chloropropyl)-benzyl chloride 2 and 2,4-pentane diode 6 via the compounds 7, 8, 9, 10 and 11); and (b) reacting the ketone XV with a selected lithium cuprate V to form the desired product XVII which may be hydrogenated to dihydro form XX.

4. Forming an $F_1$-prostaglandin analogue of Formula Ie by reducing the ketone function of the $E_1$-series analogue XVII to form the desired product XVIII which may be hydrogenated to the dihydro form XXI.

5. Forming an $A_1$-prostaglandin analogue of Formula If through dehydration of the $E_1$-series analogue XVII to form the desired product XIX.

Specific reaction parameters and variations of the syntheses outlined in Tables A–G will become apparent upon consideration of the following detailed description thereof.

As one example, the unsaturated ketones XV and the halovinyl alcohols XXII possess a free hydroxyl group that must be protected during the reaction with the lithium cuprate complex V. This is done by converting them to the mixed acetals XVI and XXIII by reaction with ethyl vinyl ether just prior to reaction [Kluge, et al., J. Amer. Chem. Soc. 94:7827 (1972); Sih, et al., J. Amer. Chem. Soc. 94:3643 (1972)]. These are isolated and used directly.

As another example, as indicated in Tables A, B and C, the reaction of the lithium cuprate complexes V derived from an optically active alcohol, XXII, with the ketones IV, IX, and XVI produces, in each case, two isomers: the so-called 15-epi-enantimomeric isomer with the stereochemistry depicted in XXXII and the natural isomer depicted in XXXIII. These can usually be separated by column chromatography.

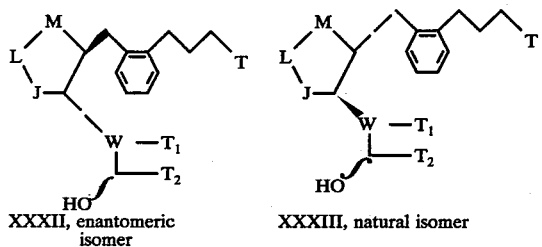

XXXII, enantomeric isomer    XXXIII, natural isomer

The 15-epi-enantomeric isomer (ent) is commonly less polar than the natural isomer (nat) and hence is eluted off the column first.

DETAILED DESCRIPTION

The following Examples 1–20 relate to preparation of certain intermediates involved in the preparation of compounds of the structure I.

EXAMPLE 1

2-[2-(3-Chloropropyl)benzyl]-1,3-cyclohexanedione, 3.

A solution of 155 g (0.75 mol) of 2-(3-chloropropyl)-benzyl chloride 2 [Page, et al., J. Amer. Chem. Soc. 75:2053 (1953)], 91 g (0.81 mol) of 1,3-cyclohexanedione I [Aldrich Chem. Co. 10,160-5; Beilstein 7, 554], and 47 g of 85% KOH in 400 ml of methanol was refluxed 16 hours. After concentrating, the residue was partitioned between benzene and dilute aqueous NaOH solution. Acidification of the aqueous phase gave a solid that was recyrstallized from ethyl acetate to give 34 g of the dione 3, mp 143°–145° C.

Analysis, Calc'd. for $C_{16}H_{19}ClO_2$: C, 68.93; H, 6.87. Found: C, 69.66; H, 7.21.

EXAMPLE 2

2-[2-(3-Cyanopropyl)benzyl]-1,3-cyclohexanedione, IIa.

A mixture of 22 g (0.079 mol) of 2-[2-(3-chloropropyl)benzyl]1,3-cyclohexanedione 3 and 15.5 g (0.316 mol) of NaCN in 250 ml of dry dimethyl sulfoxide was stirred at 95° C for 3 hours. The reaction was filtered while hot to remove NaCl, and the dimethyl sulfoxide was distilled out under high vacuum. The residue was dissolved in 400 ml $H_2O$, filtered through a diatomaceous earth filter aid (celite) to give a red solution and neutralized by the rapid addition of 40 ml concentrated HCl. The precipitate was recrystallized twice from ethyl acetate to give 16 g of the cyanodione, IIa, mp 143° C.

Analysis, Calc'd. for $C_{16}H_{19}NO_2$: C, 75.81; H, 7.11; N, 5.20.

Found: C, 76.97; H, 7.39; N, 4.86.

EXAMPLE 3

5-Keto-7-[2-(3-Carboxypropyl)benzyl]heptanoic Acid, 4.

A solution of 32 g (0.12 mol) of 2-[2-(3-cyanopropyl)-benzyl]-1,3-cyclohexanedione IIa in 250 ml glacial acetic acid and 250 ml concentrated HCl was refluxed 16 hours. The solvent was evaporated and the residue recrystallized from $H_2O$ to give 30 g of the keto diacid 4, mp 87° C.

Analysis, Calc'd. for $C_{17}H_{22}O_5$: C, 66.65; H, 7.24. Found: C, 66.52; H, 7.50.

EXAMPLE 4

Methyl 5-Keto-7-[2-(3-carbomethoxypropyl)benzyl]heptanoate, 5.

A mixture of 30 g (0.1 mol) of 5-keto-7-[2-(3-carboxypropyl)benzyl]heptanoic acid, 4, 150 ml absolute methanol, and 26 g (0.2 mol) of boron trifluoride-methanol complex was refluxed for 2 hours. The solvent was evaporated to near dryness and the gummy residue taken up in 500 ml ether. After washing to neutrality with $H_2O$ and aqueous sodium bicarbonate, the ether solution was dried over anhydrous $CaCl_2$ and evaporated. This gave 29 g of the keto diester 5 as a pale amber oil. This was not further purified but was used directly to make the dione IIb.

EXAMPLE 5

2-[2-(3-Carbomethoxypropyl)benzyl]-1,3-cyclohexanedione, IIb.

The diester 5, 26.5 g (0.08 mol) was dissolved in a solution made by dissolving 1.84 g (0.09 g-atm) sodium in 200 ml absolute MeOH. The resulting solution was refluxed 9 hours. Evaporation gave a red, gummy residue that was partitioned between 300 ml $H_2O$ and 309 ml ether. Evaporation of the ether gave back 3 g of unreacted keto diester 5. The aqueous phase was acidified and the precipitate recrystallized from toluene to give 20 g of the dione ester IIb, mp 124°–125° C.

Analysis, Calc'd. for $C_{18}H_{22}O_4$: C, 71.50; H, 7.33. Found: C, 71.31; H, 7.42.

EXAMPLE 6

2-[(3-Cyanopropyl)benzyl]-2-cyclohexene-1-one, IVa.

A solution of 39 (0.145 mol) of 2-[2-(3-cyanopropyl)-benzyl]-1,3-cyclohexanedione IIa in 500 ml of dry tetrahydrofuran (THF) and 20 ml of triethylamine was cooled to 0° C. A solution of 29 g (0.15 mol) of -toluenesulfonyl chloride in THF was added dropwise over 30 minutes. After 3 hours the precipitate of triethylamine HCl was filtered off and the filtrate evaporated at 35° C under reduced pressure. The oily residue was taken up in 500 ml ether and washed with cold 1N HCl, aqueous $NaHCO_3$ and brine. It was dired over anhydrous $MgSO_4$ and evaporated to give the enol sulfonate IIIa (Ar = $p-CH_3C_6H_4$) as an oil. This was not purified but was taken up in 500 ml absolute ethanol and cooled to 0° C. To this was added 5.7 g (0.15 mol) of solid sodium borohydride. After stirring overnight the reduction was quenched with 1 molar oxalic acid solution and concentrated to about ⅓ the volume. This was extracted with 500 ml of ether, washed with brine, dried over $MgSO_4$, and evaporated to give a tan oil. This was quickly taken up in 300 ml dry THF containing 13.5 g (0.15 mol) of oxalic acid and 20.1 g (0.15 mol) of sodium oxalate. After stirring at room temperature for one day, the solution was filtered and evaporated to dryness. This gave 35.5 g of a brown oil that was chromatographed on 600 g silicic acid and eluted with 19:1 v:v carbon tetrachloride:acetone. Like fractions were combined and evaporated to give 21 g of the cyana-ketone IVa as an oil.

Analysis, Calc'd. for $C_{17}H_{19}NO$: C, 80.59; H, 7.56; N, 5.53;
Found: C, 81.11; H, 7.67; N, 5.69;

EXAMPLE 7

2-[2-(3-Carbomethoxypropyl)benzyl]-2-cyclohexene-1-one, IVb

A solution of 2.2 g (0.009 mol) of 2-[2-(3-cycanopropyl) benzyl]-2-cyclohexene-1-one IVa in 50 ml glacial acetic acid and 50 ml concentrated HCl was refluxed 5 hours. Evaporation of the solution gave the free acid IVc as a dark oil. This was not purified but was converted to the methyl ester by heating 2 hours in 100 ml of absolute methanol containing 10 ml of boron trifluoride-methanol complex. Evaporation gave a dark oil residue that was taken up in 200 ml of ether and washed with $H_2O$, aqueous $NaHCO_3$ solution and brine. It was dried and evaporated. This crude ester was chromatographed on silica gel and eluted with 19:1 v:v carbon tetrachloride:acetone. Like fractions were combined to give 1.9 g of a clear colorless oil of the keto ester IVb.

Analysis, Calc'd. for $C_{18}H_{22}O_3$; C, 75.49; H, 7.75.
Found: C, 75.58; H, 7.62.

EXAMPLE 8

2-Chloro-2-[2-(3-cyanopropyl)benzyl]-1,3-cyclohexanedione, VIIIa.

A suspension of 15.15 g (0.056 mol) of 2-[2-(3-cyanopropyl)benzyl]-1,3-cyclohexanedione, IIa, finely ground, in 400 ml chloroform, was cooled to −20° with stirring. Over the next 2 hours, a solution of 6.1 g (0.056 mol) of freshly prepared t-butyl hypochlorite was dripped in. After 3 more hours at 0° C, the solvent was removed at 35° C under reduced pressure. The residue was recrystallized from $CCl_4$ to give 15 g of the chloro derivative VIIIa, mp 78° C.

Analysis, Calc'd. for $C_{17}H_{18}ClNO_2$: C, 67.21; H, 5.97; N, 4.61.
Found: C, 67.59; H, 6.24; N, 4.29.

EXAMPLE 9

2-[2-(3-Cyanopropyl)benzyl]-2-cyclopentene-1-one, IXa.

A mixture of 8.5 g (0.028 mol) of 2-chloro-2-[2-(3-cyano propyl)benzyl]-1,3-cyclohexanedione VIIIa, and 15 g (0.14 mol) of sodium carbonate in 200 ml of xylene was refluxed with stirring for 2 hours under argon. It was then cooled, filtered and evaporated to give a brown-yellow oil. This was evaporatively distilled at 170° C/0.01 mm to give 4 g of the cyano ketone IXa as a pale yellow oil.

Analysis, Calc'd. for $C_{16}H_{17}NO$: C, 79.05; H, 7.04; N, 5.86.
Found: C, 79.46; H, 7.43; N, 5.47.

EXAMPLE 10

2-Chloro-2-[2-(3-Carbomethoxypropyl)benzyl]-1,3-cyclohexane dione, VIIIb.

A solution of 10.5 g (0.034 mol) of 2-[2-(3-carbomethoxypropyl)benzyl]-1,3-cyclohexanedione, IIb, in 100 ml $CHCl_3$ was prepared and cooled to 0°. To this was added a solution of 4.1 g (0.034 mol) of t-butyl hypochlorite in 50 ml $CHCl_3$ and the reaction was stirred overnight at 0° C. Evaporation of the solvent left a crystalline residue. A small sample was recrystallized from $CCl_4$ to give the crystalline chloro diketone VIIIb, mp 79° C.

Analysis, Calc'd. for $C_{18}H_{21}ClO_4$: C, 64.18; H, 6.29.
Found: C, 62.85; H, 6.19.

EXAMPLE 11

2-[2-(3-Carbomethoxypropyl)benzyl]-2-cyclopentene-1-one, IXb

A mixture of 10 g (0.026 mol) of 2-chloro-2-[2-(3-carbomethoxypropyl)benzyl]-2,3-cyclohexanedione, VIIIb and 18.5 g (0.175 mol) of anhydrous $Na_2CO_3$ was refluxed in 200 ml xylene for 2 hours. Filtration and evaporation gave a brown oil (10 g). Evaporative distillation at 175° C/0.2 mm gave 6 g of a pale yellow oil. This was chromatographed on silica gel and eluted with 7:3 v:v $CCl_4$:acetone. Like fractions were combined to give 4.1 g of the keto ester IXb as a pale yellow oil.

Analysis, Calc'd. for $C_{17}H_{20}O_3$: C, 74.97; H, 7.40.
Found: C, 74.10; H, 7.38.

EXAMPLE 12

4-[2-(3-Chloropropyl)pehnyl]-2-butanone, 7

A mixture of 258 g (1.27 mol) of 2-(3-chloropropyl)-benzyl chloride, 2, 140 g (1.4 mol) of 2,4-pentanedione, 6, 175 g (1.27 mol) potassium carbonate, and 700 ml of absolute ethanol was stirred at reflux for 18 hours. Evaporation of the alcohol gave a residue which was partitioned between ether and water. The organic phase was dired over anhydrous $MgSO_4$, concentrated and the residue distilled to give the chloro ketone 7, 218 g, bp 123°–127° C/0.2 mm.

Analysis, Calc'd. for $C_{13}H_{17}ClO$: C, 69.47; H, 7.85.
Found: C,70.39; H, 7.85.

EXAMPLE 13

4-[2-(3-Cyanopropyl)phenyl]-2-butanone, 8

A solution of 218 g (0.97 mol) of 4-[2-(3-chloropropyl)phenyl]-2-butanone, 7, in 700 ml dimethyl sulfoxide containing 200 g dry sodium cyanide was heated to 100° C for 3 hours. The diemthyl sulfoxide was distilled out under high vacuum and the residue partitioned between ether and H$_2$O. The ether phase was separated, dried over anhydrous MgSO$_4$, concentrated and the residue distilled to give 164 g of the keto-nitrile 8, bp 143°-146°C/0.3 mm.

Analysis, Calc'd. for C$_{14}$H$_{17}$NO: C, 78.10; H, 7.96; N, 6.51.
Found: C, 77.83; H, 8.08; N, 6.40.

EXAMPLE 14

4-[2-(3-Carboxypropyl)phenyl]-2-butanone, 9

A solution of 50 g (0.23 mol) of 4-[2-(3-cyanopropyl)phenyl]-2-butanone, 8 in 125 ml glacial acetic acid and 125 ml concentrated HCl was refluxed overnight. The solution was evaporated and the residue diluted with H$_2$O. The precipitate was recrystallized from benzene-petroleum either to give 42.5 g of the keto acid 9, mp 59°-61° C.

Analysis, Calc'd. for C$_{14}$H$_{18}$O$_3$: C, 71.77; H, 7.74.
Found: C, 72.60; H, 7.99.

EXAMPLE 15

4-[2-(3-Carbomethoxypropyl)phenyl]-2-butanone, 10

A solution of 117 g (0.5 mol) of 4-[2-(3-carobxypropyl) phenyl]-2-butanone, 9, in 200 ml of absolute methanol containing 2 equivalents (1.0 mol) of boron trifluoride methanol complex was refluxed for 16 hours. It was concentrated and the residue washed with H$_2$O, then aqueous sodium bicarbonate solution. After drying, it was distilled to give 111 g of the keto ester 10, bp 132°-136° C/0.2 mm.

Analysis, Calc'd. for C$_{15}$H$_{20}$O$_3$: C, 72.55; H, 8.12.
Found: C, 71.71; H, 8.10.

EXAMPLE 16

2-[2-(3-Carboxypropyl)benzyl]-1,3,4-cyclopentanetrione, 11

A solution of 96 (0.44 mol) of 4-[2-(3-carbomethoxy propyl)pehnyl]-2-butanone, 10, and 129 g (0.88 mol) of diethyloxalate was added dropwise at room temperature to a solution made by dissolving 20.2 g (0.88 g-atm) sodium in 20 ml absolute ethanol. After the addition was complete, the reaction was stirred 1 hour at room temperature and 1 hour at 50° C. It was then concentrated, the residue taken up in H$_2$O, and acidified with 70 ml concentrated HCl. The precipitated material was extracted into ether and washed twice with H$_2$O. The acidic material was then extracted out of this ether phase with aqueous sodium carbonte solution. Upon acidification of the sodium carbonate solution a red oil separated. This oil was heated overnight in a solution of 200 ml concentrated HCl and 200 ml methanol. The reaction mixture was diluted with 300 ml H$_2$O and extracted with ether. Evaporation of the ether gave 70 g of red oil. This was chromatographed on 400 g silicic acid and eluted with benzene:ethanol. Like fractions were combined and crystallized. Recrystallization from benzene gave 23 g of the trione acid 11, mp 123° C.

Analysis, Calc'd. for C$_{16}$H$_{16}$O$_5$: C, 66.66; H, 5.60.
Found: C, 66.30; H, 5.58.

EXAMPLE 17

2-[2-(3-Carbomethoxypropyl)benzyl]-1,3,4-cyclopentanetrione, XIIa.

A solution of 45 g (0.16 mol) of 2-[2-(3-carboxy propyl)benzyl]-1,3,4-cyclopentanetrione, 11, in 100 ml absolute MeOH containing 10 ml concentrated HCl was stirred 24 hours at room temperature. Evaporation gave a dark residue that was taken up in either and extracted with aqueous NaHCO$_3$. Neutralization gave 40 g of crude ester. Chromatography on 1000 g silicic acid and elution with 4:1 v:v benzene:ethyl acetate gave 32 g of the trione ester XIIa as a red oil.

Analysis, Calc'd. for C$_{17}$H$_{18}$O$_5$: C, 67.54; H, 6.00; N.E. (neutralization equivalent), 302.3. Found: C, 68.71; H, 6.16; N.E., 306.3.

EXAMPLE 18

2-[2-(3-Carbomethoxypropyl)benzyl]-4-hydroxy-1,3-cyclopentane dione, XIIIa.

A toluene solution of 30.5 g (0.1 mol) of 2-[2-(3-carbomethoxypropyl)benzyl]-1,3,4-cyclopentanetrione, XIIa, was thoroughly dried by azeotropic distillation. Removal of the toluene gave a red oil that was taken up in 200 ml of 2-propanol. Five grams of Pd/C was added and the compound hydrogenated at 0.25 psi for 3 days. The catalyst was filtered and the solvent evaporated to give the crude product. This was chromatographed on silicic acid and eluted with 4:1 benzene:ethyl acetate. The major fraction amounted to 20 g of the hydroxy dione XIIIa as a clear, light tan oil.

Analyis, Calc'd. for C$_{17}$H$_{20}$O$_5$: C, 67.09; H, 6.62; N.E., 304.3. Found: C, 67.03; H, 6.85; N.E., 322.0.

EXAMPLE 19

2-[2-(3-Carbomethoxypropyl)benzyl]-4-hydroxy-2-cyclopentene-1-one, XVa.

A solution of 19 g (0.063 mol) of the hydroxydione XIIIa in 200 ml dry ether was cooled to 0° C. To this was added 10 ml triethylamine followed by a solution of 14 g (0.063 mol) of 2-mesitylenesulfonyl chloride in 50 ml of ether. After stirring 30 minutes at 0° C the solution was allowed to warm to room temperature. It was then washed with cold H$_2$O, 1N HCl, brine, then dried over anhydrous CaCl$_2$ and concentrated at 32° C under reduced pressure. The light colored oily residue of the enol sulfonate XIV$_a$ (Ar = 2,4,6—C$_6$H$_2$—) was not purified but was used directly in the next step. It was taken up in 300 ml absolute ethanol and cooled to 0° C. 2.4 g (0.063 mol) of sodium borohydride was added and the reaction stirred overnight. The reaction was then quenched with 1 molar oxalic acid, the solution concentrated to a third of its volume, and the residue partitioned between ether and H$_2$O. The ether phase was separated, dried over anhydrous MgSO$_4$, and evaporated under reduced pressure to give a brown residue. This was taken up in 100 ml dry THF and stirred with 5.7 g (0.063 mol) of oxalic acid and 8.5 g (0.063 mol) of sodium oxalate for 16 hours. Filration and evaporation gave a residue that was twice chromatographed; first on silicic acid and second on silica gel, both times eluting with 9:1 v:v benzene:ethyl acetate. This gave 5 g of the hydroxy ketone XVa as a pale yellow oil; $n_D^{19}$ = 1.5499.

Analysis, Calc'd. for $C_{17}H_{20}O_4$: C, 70.81; H, 6.99. Found: C, 70.74; H, 7.23.

EXAMPLE 20

2-[2-(3-Carboethoxypropyl)benzyl]-4-hydroxy-2-cyclopentene-1-one, XVb.

Twenty grams (0.062 mol) of 2-[2-(3-carboethoxypropyl)benzyl]-1,3,4-cyclopentanetrione, XIIv, was prepared in the same manner as the methyl ester XIIa. This was isolated but not purified. Hydrogenation of this with Pd/C gave 14 g of 2-[2-(3-carboethoxypropyl)benzyl]-4-hydroxy-1,3-cyclopentanedione XIIIb; the reduction was preformed in the same was as for the methyl ester XIIIa, previously cited. This hydroxy dione ester was converted to the desired hydroxy ene one XVb in the same way as the methyl ester XVa already cited. This gave 7 g of a clear colorless oil.

Analysis, Calc'd. for $C_{18}H_{22}O_4$: C, 71.50; H, 7.34. Found: C, 71.88; H, 7.30.

The following examples illustrate preparation of certain halovinyl alcohols useful in preparation of the cuprates V employed in preparation of compounds of structure I.

EXAMPLE 21

(E)-1-Iodo-3-(S)-hydroxy-2-phenyl-1-butene, XXXIIa.

Phenylacetone (Aldrich Chem. Co. 13,538-0; Beilstein 7, 303), XXVIa (101 g, 0.75 mol) was combined with 100 g (1.35 mol) of ethyl formate was added all at once to a suspension of 50 g (0.75 mol) of sodium ethoxide in 500 ml of THF. After 3 hours at room temperature the brown solution was diluted with 400 ml of $H_2O$. Following extraction with benzene to remove unreacted starting material, the aqueous phase was acidified with dilute HCl. The product was extracted with benzene, washed with $H_2O$, dried over $MgSO_4$, and concentrated to give an oil. Distillation gave 39 g (0.24 mol) of (Z)-1-hydroxymethylene-1-phenylacetone, XXVIIIa, as a colorless oil, bp 65–69° C (0.3 mm).

A solution of 39 g (0.24 mol) of this compound and 24 g of pyridine in 100 ml of methylene chloride was treated dropwise at 0° C with a solution of 48 g (0.25 mol) of p-toluenesulfonyl chloride and 12 g of pyridine in 75 ml of methylene chloride. After 3 hours at 0° C, the reaction was worked up to give a dark crystalline residue of (Z)-1-tosyloxymethylene-1-phenylacetone XXVIIIa. A sample was recrystallized from benzene to give white crystals, mp 8–85 (dec).

Analysis, Calc'd. for $C_{17}H_{16}SO_4$: C, 65.54; H, 5.10. Found: C, 64.95; H, 5.11.

The main portion of this tosylate was combined with a solution of 120 g (0.8 mol) of sodium iodide in 600 ml of acetone containing 3 ml of concentrated sulfuric acid. After stirring overnight at room temperature, the mixture was poured into 700 ml of $H_2O$ and the product extracted out with methylene chloride. The aqueous layer was washed with benzene and the combined organic layers dried and evaporated to give a crystalline residue of (E)-1-iodomethylene-1-phenylacetone, XXIXa. A sample of this was recrystallized from petroleum ether to give white crystals, mp 97° C.

Analysis, Calc'd. for $C_{10}H_9IO$: C, 44.14; H, 3.33. Found: C, 44.50; H, 3.40.

The main portion of this iodovinyl ketone was reduced with sodium borohydride in absolute ethanol. Work-up gave 40 g of a light yellow oil of the desired dl-(E)-1-iodo-3-hydroxy-2-phenyl-1-butene XXXa.

This racemic alcohol was not purified at this point but was resolved by the following procedure.

The crude alcohol, 20 g, was heated at 80° C for 1 hour with 22 g (0.15 mol) of phthalic anhydride in 50 ml of triethylamine. The reaction was then concentrated in vacuo and the yellow oily residue partitioned between chloroform and dilute hydrochloric acid. The organic phase was washed twice with $H_2O$, dried over $MgSO_4$, and evaporated to give a light orange oil of the hydrogen phthalate ester XXXIa. This was dissolved in ethyl acetate and treated with 18.5 g of L-(-)-α-methylbenzylamine and the resulting solution cooled overnight. The salt precipitated and after three recrystallizations from ethanol there was obtained 17 g of the α-methylbenzylammonium salt, $a_D = +26.8°$ (c 2.3, $CH_3$—OH).

Analysis, Calc'd. for $C_{26}H_{26}INO_4$: C, 57.47; H, 4.82; N, 2.58. Found: C, 57.37; H, 4.85; N, 2.49.

The above salt (16 g, 0.03 mol) was refluxed with 200 ml of 20% sodium hydroxide for 3 hours. When cool the mixture was diluted with water and extracted three times with ether. The combined ether extracts were washed with dilute HCl, then saturated $NaHCO_3$ and dried over $MgSO_4$. The ether was evaporated and the resulting oil was dried overnight under 0.05 mm vacuum. This gave 7 g of the resolved alcohol XXIIa as a colorless oil, $a_D = -14.33°$ (c 2.3, $CH_3OH$).

Analysis, Calc'd. for $C_{10}H_{11}IO$: C, 43.82; H, 4.05. Found: C, 43.90; H, 4.19.

EXAMPLE 22

(E)-2-Iodomethylene-(S)-cyclohexanol, XXIIb

As in the previous example, 200 g (2.0 mol) of cyclohexanone was reacted with ethyl formate to give 140 g of 2-hydroxymethylenecyclohexanone, XXVIIb, bp 71°–74° C (0.6 mm). Forty grams (0.32 mol) of this substance was dissolved in 150 ml $CH_2Cl_2$. containing 30 g of pyridine and treated at −5° C with a solution of 64 g (0.34 mol) of p-toluenesulfonyl chloride and 16 g of pyridine in 150 ml $CH_2Cl_2$. The reaction was stirred overnight at this temperature. Work-up in the usual manner gave the enol tosylate XXVIIIb. This was not isolated but added directly to a solution of 150 g (1.0 mol) NaI in dry acetone. After stirring overnight at room temperature this was worked up in the usual manner to give (E)-2-iodomethylenecyclohexanone, XXIXb, as a red oil. Again this was not isolated but was reduced with $NaBH_4$ in EtOH to give crystalline dl-(E)-2-iodomethylenecyclohexanol, XXXb. Recrystallization from petroleum ether gave 40 g of white needles, mp 80° C.

Analysis, Calc'd. for $C_7H_{11}IO$: C, 35.31; H, 4.66. Found: C, 35.56; H, 4.88.

Material from several runs was combined to give 60 g of the alcohol. This was converted to the hemiphthalate salt XXXIb as before to give 70 g of white crystals, mp 73° C. When treated with 24 g of L-(-)-α-methylbenzylamine this gave a salt. Two recrystallizations from methanol-ethyl acetate gave 30 g of the salt, mp 171°–172° C, $a_D = +30.4°$ (c 2.0, $CH_3OH$).

Analysis, Calc'd. for $C_{23}H_{26}INO_4$: C, 54.44; H, 5.17; N, 2.76. Found: C, 54.09; H, 5.18; N, 3.11.

Hydrolysis of this salt with 20% NaOH as in the previous example gave, after recrystallization from ligroine, 11 g of the alcohol XXIIb, mp 81° C, $a_D = -25.1°$ (c 2.0, $CH_3OH$).

Analysis, Calc'd. for $C_7H_{11}IO$: C, 35.31; H, 4.66. Found: C, 35.19; H, 4.65.

EXAMPLE 23

(E)-2-Bromomethylene-(S)-cyclooctanol, XXIIc

As in previous examples, 126 g of cyclooctanone, XXVIc, was reacted with ethyl formate to give 95 g (0.62 mol) of 2-hydroxymethylene-cyclooctanone, XXVIIc, bp 87°–92° C (0.4 mm).

This enol was dissolved in 300 ml of $CH_2Cl_2$ containing 61 g of pyridine and treated dropwise at 0° C with a solution of 120 g (0.63 mol) of p-toluenesulfonyl chloride in 100 ml of $CH_2Cl_2$ containing 30 g of pyridine. After stirring overnight at 0° C, the reaction was worked up as before to yield the enol tosylate XXVIIIc. This was not isolated but was combined directly with a solution of 150 g (1.73 mol) of lithium bromide in 400 ml of acetone containing 3 ml of concentrated $H_2SO_4$. After 1 hour of heating the reaction was worked up in the usual manner to give (E)-2-bromomethylenecyclooctanone, XXIXc, as a yellow-orange oil. A small sample was purified by evaporative sublimation at 85° C (0.5 mm).

Analysis, Calc'd. for $C_9H_{13}BrO$: C, 49.79; H, 6.03. Found: C, 48.49; H, 6.24.

The bulk of this ketone was reduced directly with $NaBH_4$ in EtOH. This gave the desired dl-(E)-2-bromomethylenecyclooctanol, XXXc, as a light yellow oil, 95 g, bp 84° C (0.2 mm).

Analysis, Calc'd. for $C_9H_{15}BrO$: C, 49.33; H, 6.90. Found: C, 49.99; H, 7.25.

This alcohol was resolved, as in the previous examples, by conversion to the half ester XXXIc and then to the salt with L-(-)-α-methylbenzylamine. Three recrystallizations of this salt from 2-propanol gave 37 g, mp 144°–145° C, $a_D = +36.0$ (c 2.0, $CH_3OH$).

Analysis, Calc'd. for $C_{24}H_{30}BrNO_4$: C, 61.47; H, 6.19; N, 2.87. Found: C, 61.30; H, 6.28; N, 2.80.

This was hydrolyzed with 20% NaOH as before to give after recrystallization from ligroine, the alcohol XXIIc, mp 54° C. $a_D = +7.0$ (c 2.0, $CH_3OH$).

Analysis, Calc'd. for $C_9H_{15}BrO$: C, 49.33; H, 6.90. Found: C, 50.27; H, 7.29.

EXAMPLE 24

3-(S)-Hydroxy-1-iodo-1-(E) Octene XXIId

This compound was prepared and resolved as described in Kluge, et al., J. Amer. Chem. Soc. 94:7827 (1972).

The following Examples are illustrative of the preparation of compounds of structures I of the invention. Unless otherwise indicated in the recitation of physical properties of the exemplary compounds, the optical rotation analysis was performed in methanol, c 1.0 to 2.0 and thin layer chromatographic analysis was performed in the manner of Srivastava, et al., Lipids 8:592(1973) on Merck 20 × 20cm silica gel 60 plates.

EXAMPLES 25–26

Methyl 4-2'-{[2S-(3S-hydroxy-1E-octenyl)-3R-hydroxy-5-oxocyclo-pent-1R-yl]methyl}phenylbutanoate (5,6-Dinor-4,7-inter-o-phenyleneprostaglandin $E_1$ methyl ester; Tr. No. 4250)

Methyl 4-2'-{[2S-(3S-hydroxy-1E-octenyl)-3S-hydroxy-5-oxocyclo-pent-1R-yl]methyl}phenylbutanoate (Ent-15-epi-5,6-dinor-4,7-inter-o-phenylene prostaglandin $E_1$ methyl ester; Tr. No. 4251)

Eleven ml of 2.1 molar t-butyl lithium solution in pentane was placed in a 50 ml round bottom flask equipped with magnetic stirrer, argon inlet and outlet, dropping funnel and thermometer. It was cooled to −78° C and stirred. To this was added, dropwise over a 20 minute period, 3.26 g (0.01 mole) of (E)-3(S)-(1-ethoxyethoxy-1-iodo-1(E)octene (XXIIId, wherein $T_2' = n-C_5H_{11}'T_1 = H$). An exothermic reaction occurred accompanied by the formation of a white precipitate. After an additional 20 minutes at −78° C, this mixture was added to a second solution, also at −78° C, made by dissolving 1.3 g (0.01 mol) of cuprous n-propyl acetylide and 3.26 g (0.02 mol) of hexamethylphosphorous triamide (reference insert 2b) in 10 ml of ether. This gave a dark red-brown mixture. To this was added 1.24 g (0.0034 mol) of 2-[2-(3-carbomethoxypropyl)benzyl]-4-(1-ethoxyethoxy)-2-cyclopentene-1-one(XVIa wherein T = $COOCH_3$) in 5 ml of ether. The color of the reaction lightened somewhat and it was stirred at −30° C for 2 hours. At the end of this time the reaction was quenched by pouring it into 200 ml of 1 molar ammonium sulfate solution and stirring for 20 minutes. After filtration through a diatomaceous earth filter aid the ether phase was separated and washed with $H_2O$, saturated $NaHCO_3$, and brine. The ether was removed under reduced pressure, the oily residue taken up in 200 ml of 65% aqueous acetic acid, then stirred at 35° C for 2 hours. Evaporation of solvent gave a light brown oil that was taken up in 100 ml of ether and washed successively with $H_2O$, saturated $NaHCO_3$ solution and brine. After drying over anhydrous $CaCl_2$, the ether was removed to give a light colored oil of the two isomers of XVIIa.

This mixture was chromatographed on 50 g silica gel and eluted with 4:1 v:v benzene:ethyl acetate. About 200 ml of void volume was discarded, then 15 ml fractions were collected.

Fractions 190–310 were combined and evaporated to give 440 mg of a light tan oil of the compound of structure XVIIa(Id, wherein T = $COOCH_3$; $T_1$ = H; and $T_2$ = n-$C_5H_{11}$) as the ent isomer (Tr. No. 4251: $[a]_D$ + 54.8, rf = 0.48) having the following physical characteristics:

NMR ($CDCl_3$): δ 3.6(3H,s); 5.4(2H,m); 7.1(4H,s)

Mass. Spectrum (70 eV)m/e: 416 ($M^+$)

Fractions 341–470 were combined and evaporated to give 400 mg of the compound of structure XVIIa as the nat isomer (Tr. No. 4250: $[a]_D$ = 67.3; rf = 0.45).

EXAMPLE 26A 4-2'-{[2S-(3S-Hydroxy-1E-Octenyl)-3R-hydroxy-5-oxocyclopent-1R-yl]methyl}phenylbutanoic acid (5,6-Dinor-4,7-inter-o-phenyleneprostaglandin E; Tr. No. 4730)

A phosphate buffer of approximate pH 7.4 was prepared by dissolving 4.7 g of sodium dihydrogen phosphate monohydrate and 25 g of disodium hydrogen phosphate in 1 liter of deionized water at 37° C. To this well-stirred solution was added 10 mg of the enzyme hog liver carboxylic ester hydrolase (EC 3.1.1.1, from Sigma Chemical Company) followed by 250 mg of methyl 4-2'-{[2S-3S-hydroxy-1E-octenyl)-3R-hydroxy-5-oxocyclo-pent-1R-yl]methyl}phenylbutanoate (Tr. No. 4250 of Example 25) dissolved in 10 ml of absolute methanol. A milky solution resulted which gradually became clear over the next 20 minutes. After one hour, the temperature was lowered to 5° C and the pH of the solution adjusted to 2 with dilute HCl. The reaction mixture was extracted with two 250 ml portions of ethyl acetate. These were combined, dried over anhydrous $MgSO_4$, filtered and evaporated. The crude product so obtained was chromatographed on 50 g silica gel and eluted with 9:1 v:v benzene:methanol. Ten ml fractions were collected and fractions 8 to 25 were combined to yield 170 mg of the desired acid as a pale yellow oil of structure XVIIc (Tr. No. 4730: $[\alpha]_D = -54.5°$; rf=0.32) having the following physical characteristics:

NMR ($CDCl_3$): δ 7.1 (4H,s); 5.9 (2H,m); 0.9 (3H,m).
Mass Spectrum (70 eV) m/e: 366 ($M^+ - 2H_2O$).

EXAMPLES 27–28

Methyl 4-2'-{[2S-(3S-Hydroxy-1E-octenyl)-6-oxocyclohex-1S-yl]methyl}phenylbutanoate (11-Deoxy-ent-15-epi-9a-homo-5,6-dinor-4,7-inter-o-phenylene-prostaglandin $E_1$ methyl ester; Tr. No. 4211)

Methyl 4-2'-{[2R-(3S-hydroxy-1E-octenyl)-6-oxocyclohex-1R-yl]methyl{phenylbutanoate (11-Deoxy-9a-homo-5,6-dinor-4,7-inter-o-phenylene-prostaglandin $E_1$ methyl ester; Tr. No. 4212)

Upon selection of suitable reactants, the general procedure of Examples 25–26 yielded the title compounds of structure VIb (Ib, wherein: T = $COOCH_3$; $T_1$ = H; and $T_2$ = n-$C_5H_{11}$) either as the ent isomer (Tr. No. 4211: $[\alpha]_D = +14.66$; rf = 0.70) or the nat isomer (Tr. No. 4212: $[\alpha]_D = -8.98$; rf = 0.67) having the following physical characteristics:

NMR ($CDCl_3$): δ 3.6(3H,s); 5.5(2H,m); 7.1(4H,s)
Mass Spectrum (70 eV) m/e: 414 ($M^+$)

EXAMPLES 29–30

4-2'-{[2S-(2S-hydroxy-1E-octenyl)-6-oxocyclohex-1S-yl]methyl}-phenylbutanenitrile (11-Deoxy-ent-15-epi-9a-homo-2-decarboxy-2-cyano-5,6-dinor-4,7-inter-o-phenyleneprostaglandin $E_1$; Tr. No. 4213)

4-2'-{[2R-(2S-hydroxy-1E-octenyl)-6-oxocyclohex-1R-yl]methyl}phenylbutanenitrile (11-Deoxy-9a-homo-2-decarboxy-2-cyano-5,6-dinor-4,7-inter-o-phenyleneprostaglandin $E_1$; Tr. No. 4214)

Upon selection of suitable reactants, the general procedure of Examples 25–26 yielded the title compounds of structure VIa (Ib, wherein: T = CN; $T_1$ = H; and $T_2$ = n-$C_5H_{11}$) either as the ent isomer (Tr. No. 4213: $[\alpha]_D = +16.2$; rf = 0.70) or the nat isomer (Tr. No. 4214: $[\alpha]_D = -2.1$; rf = 0.65) having the following physical characteristics:

NMR ($CDCl_3$): δ 0.9(3H,m); 5.5(2H,m); 7.1(4H,s)
Mass Spectrum (70 eV) m/e: 381 ($M^+$)

EXAMPLES 31–32 methyl 4-2'-{[2S-(2S-hydroxy-E-cyclohexylidenemethyl)-6-oxocyclohex-1S-yl]methyl}-phenylbutanoate (11-Deoxy-ent-15-epi-9a-homo-14,19-cyclo-5,6,20-trinor-4,7-inter-o-phenyleneprostaglandin $E_1$ methyl ester; Tr. No. 4230)

methyl 4-2'-{[2R-(2S-hydroxy-E-cyclohexylidenemethyl)-6-oxocyclohex-1R-yl]methyl}phenylbutanoate (11-Deoxy-9a-homo-14,19-cyclo-5,6,20-trinor-4,7-inter-o-phenyleneprostaglandin $E_1$ methyl ester; Tr. No. 4231)

Upon selection of suitable reactants, the general procedure of Examples 25–26 yielded the title compounds of structure VIB (Ib, wherein: T = $COOCH_3$; $T_1$ and $T_2$ = —($CH_2$)$_4$—) either as the ent isomer (Tr. No. 4230: $[\alpha]_D = +42.0$; rf = 0.64) or the nat isomer (Tr. No. 4231: $[\alpha]_D = -36.4$; rf = 0.62) having the following physical characteristics:

NMR ($CDCl_3$): δ 3.7(3H,s); 5.3(1H,m); 7.2(4H,s)
Mass Spectrum (70 eV) m/e: 384 ($M^+$)

EXAMPLES 33–34 methyl 4-2'-{[2S-(3S-hydroxy-1E-octenyl)-5-oxocyclopent-1S-yl]methyl}-phenylbutanoate (11-Deoxy-ent-15-epi-5,6-dinor-4,7-inter-o-phenylene-prostaglandin $E_1$ methyl ester; Tr. No. 4267)

methyl 4-2'-{[2R-(3S-hydroxy-1E-octenyl)-5-oxocyclopent-1R-yl]methyl}phenylbutanoate (11-Deoxy-5,6-dinor-4,7-inter-o-phenyleneprostaglandin $E_1$ methyl ester; Tr. No. 4266)

Upon selection of suitable reactants, the general procedure of Examples 25–26 yielded the title compounds of structure Xb (Ic, wherein: T = $COOCH_3$; $T_1$ = H; and $T_2$ = n-$C_5H_{11}$) either as the ent isomer (Tr. No. 4267: $[\alpha]_D = +29.4$; rf = 0.68) or the nat isomer (Tr. No. 4266: $[\alpha]_D = -40.5$; rf = 0.63) having the following NMR (CDCl$_3$): δ 0.9(3H,t,J=4Hz); 3.6(3H,s); 5.4(2H,m); 7.2(4H,s)
Mass Spectrum (70 eV) m/e: 400 (M+)

EXAMPLE 35 methyl
4-2'-{[2S-(3R-hydroxy-2-phenyl-1E-butenyl)-5-oxocyclopent-1S-yl]methyl}-phenylbutanoate (11-deoxy-epi-5,6-dinor-4,7-inter-14-phenyl-o-phenylene-tetranorprostaglandin E$_1$ methyl ester; Tr. No. 4298)

Upon selection of suitable reactants, the general procedure of Examples 25–26 yielded the title compound of structure Xb (Ic, wherein: T = COOCH$_3$; T$_1$= C$_6$H$_5$; and T$_2$= CH$_3$) as a mixture of isomers (Tr No. 4298: [α]$_D$ = +11.2; rf = 0.64) which could not be separated, having the following physical characteristics:
NMR (CDCl$_3$): δ 3.1(2H,q,J=2Hz); 3.3(3H,s); 6.5(1H,m); 6.7(4H,s)
Mass Spectrum (70 eV) m/e: 420 (M$^{30}$)

EXAMPLES 36–37

42-2'-{[2S-(3S-hydroxy-1E-octenyl)-5-oxocyclopent-1S-yl]methyl}-phenylbutanenitrile (11-Deoxy-ent-15-epi-2-decarboxy-2-cyano-5,6-dinor4,7-inter-o-phenyleneprostaglandin E$_1$; Tr. No. 4303)

4-2'-{[2R-(3S-hydroxy-1E-oxtenyl)-5-oxocyclopent-1R-yl]methyl}phenylbutanenitrile (11-Deoxy-2-decarboxy-2-cyano-5,6-dinor-4,7-inter-o-phenyleneprostaglandin E$_1$; Tr. No. 4302)

Upon selection of suitable reactants, the general procedure of Examples 25–26 yielded the title compounds of structure Xa (Ic, wherein: T = CN; T$_1$ = H; and T$_2$ = n-C$_5$H$_{11}$) either as the ent isomer (Tr. No. 4303: [α]$_D$ = +45.5; rf = 0.65) or the nat isomer (Tr. No. 4302: [α]$_D$ = −46.3; rf = 0.59) having the following physical characteristics:
NMR (CDCl$_3$): δ 1.1(3H,t,J=4Hz); 5.5(2H,m); 7.3(4H,s)
Mass Spectrum (70 eV) m/e: 367 (M+)

EXAMPLES 38–39 methyl
4-2'-{[2S-(2S-hydroxy-E-cyclohexylidenemethyl)-5-oxocyclopent-1S-yl]methyl}-phenylbutanoate (11-Deoxy-ent-15-epi-14,19-cyclo-5,6,20-trinor-4,7-inter-o-phenyleneprostaglandin E$_1$methyl ester; Tr. No. 4305)

methyl
4-2'-{[2R-(2S-hydroxy-E-cyclohexylidenemethyl)-5-oxocyclopent-1R-yl]methyl}phenylbutanoate (11-Deoxy-14,19-cyclo-5,6,20-trinor-4,7-inter-o-phenyleneprostaglandin E$_1$ methyl ester; Tr. No. 4304)

Upon selection of suitable reactants, the general procedure of Examples 25–26 yielded the title compounds of structure Xb (Ic, wherein: T = COOCH$_3$; T$_1$ and T$_2$ = —(CH$_2$)$_4$—) either as the ent isomer (Tr. No. 4305: [α]$_D$ = +71.0; rf = 0.62) or the nat isomer (Tr. No. 4304: [α]$_D$= −61.7; rf = 0.58) having the following physical characteristics:
NMR (CDCl$_3$): δ 3.6(3H,s); 5.1(1H,d); 7.0(4H,s)
Mass Spectrum (70 eV) m/e: 384 (M+)

EXAMPLE 40

4-2'-{[2S-(2R-hydroxy-E:cyclooctylidinemethyl)-3S-hydroxy-5-oxocyclopent-1S-yl]methyl}phenylbutanoate (ent-14,20-methylene-5,6-dinor-4,7-inter-o-phenyleneprostaglandin E$_1$ ethyl ester; Tr. No. 4513)

Upon selection of suitable reactants, the general procedures of Examples 25–26 yielded the title compound of the structure XVIIb (Id, wherein: T = COOC$_2$H$_5$; T$_1$ and T$_2$ = —(CH$_2$)$_6$—) as the ent (but not 15-epi) isomer (Tr. No. 4513: [α]= +109.8; rf = 0.58) having the following physical characteristics:
NMR (CDCl$_3$): δ 1.2(3H,t,J=7Hz); 4.1(2H,d,J=7Hz); 5.1 (1H,d,J=9Hz); 7.2(4H,s)
Mass Spectrum (70 eV) m/e: 384 (M+)

EXAMPLES 41–44 ethyl
4-2'-{[2R-(3S-hydroxyl-1E-octenyl)-5-oxo-3-cyclopenten-1R-yl]methyl}phenylbutanoate (5,6-dinor-4,7-inter-o-phenyleneprostaglandin A$_1$ ethyl ester; Tr. No. 4310)

ethyl
4-2'-{[2S-(3S-hydroxyl-1E-octenyl)-5-oxo-3-cyclopenten-1S-yl]methyl}phenylbutanoate (ent-15-epi-5,-dinor-4,7-inter-o-phenyleneprostaglandin A$_1$ ethyl ester; Tr. No. 4311)

ethyl
4-2'-{[2S-(3S-hydroxy-1E-octenyl)-3S-hydroxy-5-oxocyclopent-1S-yl]methyl}phenylbutanoate (ent-15-epi-5,6-dinor-4,7-inter-o-phenyleneprostaglandin E$_1$ ethyl ester; Tr. No. 4318)

ethyl
4-2'-{[2R-(3S-hydroxy-1E-octenyl)-3R-hydroxy-5-oxocyclopent-1R-yl]methyl}phenylbutanoate (5,6-dinor-4,7-inter-o-phenyleneprostaglandin E$_1$ ethyl ester; Tr. No. 4309)

A solution of 100 ml of 0.96 molar t-butyl lithium in n-pentane was placed in a 250 ml round bottom flask fitted with an argon inlet, dropping funnel, magnetic stirring bar, thermometer, and plastic cannula. The solution was cooled to −78°C and a second solution of 13.7 g (0.042 mol) of (E)-3-(S)-(1-ethoxyethoxy)-1-iodo-1-octene, (XXIIId) in 13 ml of dry ether was slowly added over a 30 minute period. After 30 more minutes this mixture containing the lithio derivative XXIVd, was pumped through the cannula into a second solution (also at −78°C) made by dissolving 5.5 g (0.042 mol) of cuprous n-propylacetylide in 45 ml of dry ether containing 13.7 g (0.084 mol) of hexamethylphosphorous triamide. After 20 minutes stirring at −30°C this consisted of a red solution of the lithium cuprate Vd. To it was added a solution of 5.2 g (0.014 mol) of 2-[2-(3-carboethoxypropyl)benzyl]-4-(1-ethoxyethoxy)-2-cyclopenten-1one XVIb (T$_1$ = H, T$_2$ = n-C$_5$H$_{11}$) in 23 ml of dry ether. After stirring 2 hours at −30° C, the reaction was quenched by pouring it into 1 liter of 1 molar aqueous NH$_4$Cl solution and stirring for 20 minutes. The layers were then separated and the aqueous layer extracted with two 100 ml portions of ether. The combined ether extracts were dried over anydrous MgSO$_4$ and concentrated under reduced pressure to give an oil. This oil was stirred at 37° C with 400 ml of 60% aqueous acetic acid for three hours, filtered, and concentrated under reduced pressure to give an oil. The oil was taken up in ether and washed with saturated NaHCO$_3$ solution, H$_2$O, and brine. It was dried and evaporated and the oil that resulted was chromatographed on 250 g of silica gel. Elution was with 4:1 v:v benzene:ethyl acetate and 20 ml fractions were collected.

Fractins 221–235 were combined to give 570 mg of an oil of the compound of structure XIXb (Ie, wherein: T = COOC$_2$H$_5$; T$_1$ = H; T$_2$ = n-C$_5$H$_{11}$) as the ent isomer (Tr. No. 4311: $[\alpha]_D$ = −95.2; rf = 0.55 in 4:1, v:v, benzene:ethyl acetate) having the following physical characteristics:
NMR (CCl$_4$): δ 4.1(5H,q); 5.2(2H,dd); 6.1(1H,dd); 7.1(4H,s); 7.3(1H,dd)
Mass Spectrum (70 eV) m/e: 412 (M$^+$)

Fractions 251 to 265 were combined to give 300 ml of the compound of structure XIXb as the nat isomer (Tr. No. 4310: $[\alpha]_D$ = +90.5; rf = 0.51 in 4:1, v:v, benzene:ethyl acetate).

Fractions 361 to 665 were combined to give 300 g of an oil of the compound of structure XIIb (Id, wherein: T = COOC$_2$H$_5$; T$_1$ = H; and T$_2$ = n-C$_2$H$_5$) as the ent isomer (Tr. No. 4318: $[\alpha]_D$ = +57.3; rf = 0.35 in 4:1, v:v, benzene:ethyl acetate) having the following physical characteristics:
NMR (CCl$_4$): δ 4.1(2H,q); 5.4(2H,m); 7.1(4H,s)
Mass Spectrum (70 eV) m/e: 430 (M$^+$)

Fractions 691 to 820 were combined to yield 740 mg of the compound of structure XIIb as the nat isomer (Tr. No. 4309: $[\alpha]_D$ = −58.7; rf = 0.28 in 4:1, v:v, benzene:ethyl acetate).

EXAMPLE 45 methyl 4-2'-{[2R-(3S-hydroxyoctyl)-5-oxocyclopent-1R-yl]methyl}-phenylbutanoate (11-Deoxy-13,14-dihydro-5,6-dinor-4,7-inter-o-phenylene prostaglandin E$_1$ methyl ester; Tr. No. 4269)

150 mg (0.0004 mol) of the nat isomer compound of Example 34 (Tr. No. 4266) was dissolved in 50 ml of absolute methanol, 50 mg of PtO$_2$ was added, and hydrogenation effected at 30 psig hydrogen pressure for 6 hours at room temperature. The catalyst was filtered and the solvent evaporated to give 150 mg of an oil that was chromatographed on 10 g silica gel and eluted with 9:1, v:v, benzene-ethyl acetate. 10 ml fractions were collected. Fractions 18 to 36 were combined to give 80 mg of a clear white oil of the compound of structure XIb (Ic, wherein: T = COOCH$_3$; T$_1$ = H; and T$_2$ = n-C$_5$H$_{11}$) as the nat isomer (Tr. No. 4269: $[\alpha]_D$ = +5.01; rf = 0.38 in 4:1, v:v, CCl$_4$:acetone) having the following physical characteristics:
NMR (CCl$_4$): δ 0.9(3H,t,J=4Hz); 3.6(3H,s); 7.1(4H,s)
Mass Spectrum (70 eV) m/e: 402 (M$^+$)

EXAMPLE 46 methyl 4-2'-{[2S-(3S-hydroxyoctyl)-5-oxocyclopent-1S-yl]methyl}-phenylbutanoate (11-Deoxy-13,14-dihydro-ent-15-epi-5,6-dinor-4,7-inter-o-phenyleneprostaglandin E$_1$ methyl ester; Tr. No. 4297)

The title compound is secured in the manner of Example 45 when the ent isomer of Example 33 (Tr. No. 4267) is employed as the starting compound. Thus hydrogenation of 150 mg of the selected starting compound yielded 57 mg of its dihydro analogue of the structure XIb (Ic, wherein: T = COOCH$_3$; T$_1$ = H; and T$_2$ = n-C$_5$H$_{11}$) as the ent isomer (Tr. No. 4297: $[\alpha]_D$ = −17.43; rf = 0.34 in 4:1 CCl$_4$:acetone) having the following physical characteristics:
NMR (CCl$_4$): δ 0.9(3H,t,J=4Hz); 3.6(3H,s); 7.1(4H,s)
Mass Spectrum (70 eV) m/e: 402 (M$^+$)

EXAMPLE 47

4-2'-{[2R-(3-hydroxy-1E-octenyl)-5-oxocyclopent-1R-yl]methyl}-phenylbutanoic acid (11-Deoxy-5,6-dinor-4,7-inter-o-phenyleneprostaglandin E$_1$; Tr. No. 4399)

A solution of 600 mg (0.0015 mol) of the nat isomer compound of Example 34 (Tr. No. 4266) in 2.5 ml of MeOH was combined with 4.5 ml of 5% KOH in 3:1, v:v, MeOH:H$_2$O. After stirring for 3 hours the reaction solution was concentrated to dryness at 32° C under reduced pressure. The residue was partitioned between 25 ml of ether and 25 ml H$_2$O. Acidification of the aqueous phase with 2% H$_2$SO$_4$ was followed by extraction with ether. Evaporation of the ether gave 387 mg of a cloudy oil. This was chromatographed on 15 g of silica gel and eluted with 19:1, v:v, benzene:ethanol. About 30 ml of void volume was discarded, then 10 ml fractions were collected.

Fractions 4–18 were combined and evaporated to give 290 mg of a pale yellow oil of the compound of structure Xc (Ic, wherein: T = COOH; T$_1$ = H; and T$_2$ = n-C$_5$H$_{11}$) as the nat isomer (Tr. No. 4399: $[\alpha]_D$ = −45.8; rf = 0.51 in 3:2, v:v, CCl$_4$:acetone) having the following physical characteristics:
NMR (CCl$_4$): δ 3.9(1H,bs); 5.4(2H,bs); 7.0(4H,s); 7.2(1H,s)
Mass Spectrum (70 eV) m/e: 386 (M$^+$)

EXAMPLE 48

4-2'-{[2S-(3S-hydroxy-1E-octenyl)-5-oxocyclopent-1S-yl]methyl}-phenylbutanoic acid (11-Deoxy-ent-15-epi-5,6-dinor-4,7-inter-o-phenyleneprostagladin E$_1$; Tr. No. 4400)

The title compound is secured in the manner of Example 47 when the ent isomer compound of Example 33 (Tr. No. 4267) is employed as the starting compound. Thus hydrolysis of 600 mg of the selected starting compound yielded 200 mg of its acid analogue of the structure Xc (Ic, wherein: T = COOH; T$_1$ = H; and T$_2$ = n-C$_5$H$_{11}$) as the ent isomer (Tr. No. 4400: $[\alpha]_D$ = +41.3; rf = 0.56 in 3:s, v:v, CCl$_4$:acetone) having the following physical characteristics:
NMR (CCl$_4$): δ 3.0(1H,bs); 5.5(2H,m); 7.0(4H,s); 7.2(1H,s)
Mass Spectrum (70 eV) m/e: 386 (M$^+$)

EXAMPLES 49–50 ethyl
4-2'-{[2R-(3S-hydroxy-1E-octenyl)-3R,5S-dihydroxycyclopent-1R-yl]methyl}phenylbutanoate (5,6-dinor-4,7-inter-o-phenyleneprostaglandin $F_{1\alpha}$ ethyl ester; Tr. No. 4321)

ethyl
4-2'-{[2R-(3S-hydroxy-1E-octenyl)-3R,5R-dihydroxycyclopent-1R-yl]methyl}phenylbutanoate (5,6-dinor-4,7-inter-o-phenyleneprostaglandin $F_{1\beta}$ ethyl ester; Tr. No. 4322)

A solution of 650 mg (0.0015 mol) of 5,6-dinor-4,7-inter-o-phenyleneprostaglandin $E_1$ ethyl ester (Tr. No. 4309 prepared in the manner of Example 44) in 25 ml of ethanol was cooled to −23° C with stirring. A cold (−23° C) slurry of 1.35 g (0.035 mol) of sodium borohydride in 25 ml of ethanol was added all at once. After 20 minutes the reaction was quenched by adding 1.5 ml acetic acid dissolved in 50 ml $H_2O$. 100 ml of ether was added and the mixture stirred for 1 hour. The layers were then separated. The ether phase was washed twice with brine, dried over anhydrous $MgSO_4$, and concentrated under reduced pressure to give 480 mg of an oil. This oil was taken up in 10:1:0.006, v:v:v, $CHCl_3$:$C_2H_5OH$:$H_3BO_3$ and chromatographed on 25 g of silica gel. Elution was with the solvent mixture just described and 1 ml fractions were collected.

Fractions 5 to 10 contained 220 mg of an oil of the compound of structure XVIIb (If, wherein: T = $COOC_2H_5$; $T_1$ = H; and $T_2$ = n-$C_5H_{11}$) as the ent (9-epi) isomer (Tr. No. 4322: $[\alpha]_D$ = −1.78; rf = 0.22 in 100:1)0.006, v:v:v, $CHCl_3$:$C_2H_5OH$:$H_3PO_3$) having the following physical characteristics:

NMR ($CCl_4$): δ 4.1(2H,q); 5.4(2H,m); 7.1)4H,s)
Mass Spectrum (70 eV) m/e: 414 (M+)

Fractions 13 to 20 contained 230 mg of an oil of the compound of structure XVIIb (If, wherein: T = $COOC_2H_5$ $T_1$ = H; and $T_2$ = n-$C_5H_{11}$) as the nat isomer (Tr. No. 4321: $[\alpha]_D$ = +20.3; rf = 0.16 in 10:1:0.006, v:v:v, $CHCl_3$:$C_2H_5OH$:$H_3PO_3$.

EXAMPLES 51–52 ethyl
4-2'-{[2S-(3S-hydroxy-1E-octenyl)-3S,5S-dihydroxycyclopent-1S-yl]methyl}phenylbutanoate (ent-15-epi-5,6-dinor-4,7-inter-o-phenyleneprostaglandin $F_{1\beta}$ ethyl ester; Tr. No. 4323)

ethyl
4-2'-{[2S-(3S-hydroxy-1E-octenyl)-3S,5R-dihydroxycyclopent-1S-yl]methyl}phenylbutanoate (ent-15-epi-5,6-dinor-4,7-inter-o-phenyleneprostaglandin $F_{1\alpha}$ ethyl ester: Tr. No. 4324)

300 mg of the ent isomer compound of structure XIIb (Tr. No. 4318) prepared according to Examples 41–44 was reduced according to the procedure of Examples 49–50 to give 100 mg of oil of the compound of structure XVIIb (If, wherein: T = $COOC_2H_5$; $T_1$ = H; $T_2$ = n-$C_5H_{11}$) as the 9,15-epi-ent isomer (Tr. No. 4323: $[\alpha]_D$ = −3.39; rf=0.27 in 10:1:0.06, v:v:v, $CHCl_3$: $C_2H_5OH$:$H_3PO_3$) having the following physical characteristics:

NMR ($CCl_4$): δ 4.0(2H,q); 5.4(2H,m); 7.0(4H,s)
Mass Spectrum (70 eV) m/e: 414 (M+)

Also yielded was 200 mg. of oil of structure XVIIb, as above, but as the 15-epi-ent isomer (Tr. No. 4324: $[\alpha]_D$ = +16.05; rf=0.20 in 10:1:0.06, v:v:v, $CHCl_3$:$C_2H_5OH$:$H_3PO_3$).

EXAMPLE 53

4-2'-{[2R-(3S-hydroxy-1E-octenyl)-3R,5S-dihydroxycyclopent-1R-yl]methyl}phenylbutanoic acid (5,6-dinor-4,7-inter-o-phenyleneprostaglandin $F_{1\alpha}$: Tr. No. 4428)

One hundred mg of the nat isomer of Examples 49–50 was hydrolyzed by the procedure of Example 47 to prepare 70 mg of the desired acid of structure XVIIc (If, wherein: T = COOH; $T_1$ = H; and $T_2$ = n-$C_5H_{11}$) as the nat isomer (Tr. No. 4428: $[\alpha]_D$ = −22.6; rf = 0.12 in 10:1:0.06, v:v:v, $CHCl_3$: $C_2H_5OH$:$H_3PO_3$) having the following physical characteristics:

NMR ($CDCl_3$): δ 5.3(2H,bd); 7.1(4H,s)
Mass Spectrum (70 eV) m/e: 386 (M+-$H_2O$)

EXAMPLE 54

4-2'-{[2R-(3S-hydroxy-1E-octenyl)-5-oxo-3-cyclopenten-1R-yl]methyl}phenylbutanoic acid (5,6-dinor-4,7-inter-o-phenyleneprostaglandin $A_1$; Tr. No. 4410)

One hundred mg of the nat isomer of structure XIXb of Examples 41–44 (Tr. No. 4310) was emulsified in 8 ml of 10% gum arabic and placed in a water bath at 37° C. To this was added 0.6 ml of 20% aqueous sodium deoxycholate solution and the pH adjusted to 7.8 with 0.1 N NaOH. Then 100 mg of the enzyme hog pancreatic lipase in 2 ml $H_2O$ was added. The pH of the reaction was maintained at 7.8 by the addition of 0.1 N NaOH as needed during the first hour. After one hour, 100 mg of fresh enzyme was added and the reaction allowed to stir overnight. The pH was then adjusted to 3.0 with 10% HCl and the mixture extracted with chloroform. The chloroform extract was dried over anhydrous $MgSO_4$ and concentrated under reduced pressure to give an oil. This was chromatographed on 10 g of silica gel and eluted with 9:1, v:v, $CCl_4$:acetone. Two-ml fractions were collected.

Fractions 48 to 78 yielded 80 mg of the desired acid of structure XIXc (Ie, wherein: T = COOH; $T_1$ = H; $T_2$ = n-$C_5H_{11}$) as the nat isomer (Tr. No. 4410; $[\alpha]_D$ = +35.1; rf = 0.05 in 4:1, v:v, $CCl_4$:acetone) having the following physical characteristics:

NMR ($CCl_4$): δ 5.2(2H,m); 7.1(4H,m); 7.2(1H,m)
Mass Spectrum (70 eV) m/e: 384 (M+)

EXAMPLE 55

Compounds of the invention exhibit selective biological activities and were evaluated, inter alia, for their effect on human platelet aggregation in vitro.

The ability of test compounds to inhibit platelet aggregation was determined by a modification of the turbidometric technique of Born [Nature, 194:927 (1962)]. Blood was collected from human volunteers who had not ingested aspirin or aspirin-containing products within the preceding two weeks in heparinized containers and was allowed to settle for one (1) hour. The platelet rich plasma (prp) supernates were collected and pooled. Siliconized glassware was used throughout.

In a representative assay 1.9 ml of PRP and 0.2 ml of test compound at the appropriate concentration (0.001 to 100 mc/gm), or 0.2 ml of distilled water (control procedure) were placed in sample cuvettes. The cuvettes were placed in a 37° C incubation block for 15 minutes, and then in a spectrophotometer linked to a strip chart recorder. After 30-60 seconds, 0.2 ml of a solution, prepared by diluting a calf-skin collagen solution 1:9 with Tyrodes' Solution, was added to each cuvette. Platelet aggregation was evidenced bu a decrease in optical density.

Calculation of the degree of inhibition of platelet aggregation exhibited by each concentration of test compound was accomplished according to the method of Caprino et al., [Arzneim-Forsch., 23:1277 (1973)]. An $ED_{50}$ value was then determined graphically. Activity of the compounds was scored as follows:

| $ED_{50}$ (mcg/kg) | Activity Value |
|---|---|
| >1.0 | 0 |
| >0.1 <1.0 | 1 |
| >0.1 ≦0.1 | 2 |

Table H summarizes the results of the preceding screen using the preferred examples.

TABLE H

Summary of Biological Activity Screen for Platelet Aggregation

| TR No. | Example No. | Activity Value Platelet Aggregation |
|---|---|---|
| 4211 | 27 | 1 |
| 4212 | 28 | 1 |
| 4213 | 29 | 1 |
| 4214 | 30 | 1 |
| 4230 | 31 | 1 |
| 4231 | 32 | 1 |
| 4310 | 41 | 1 |
| 4311 | 42 | 1 |
| 4410 | 54 | 1 |
| 4269 | 45 | 0 |
| 4297 | 46 | 1 |
| 4250 | 25 | 1 |
| 4251 | 26 | 1 |
| 4730 | 26A | |
| 4309 | 44 | 1 |
| 4318 | 43 | 1 |
| 4266 | 34 | 1 |
| 4267 | 33 | 1 |
| 4302 | 37 | 1 |
| 4303 | 36 | 1 |
| 4304 | 39 | 1 |
| 4305 | 38 | 1 |
| 4399 | 47 | 1 |
| 4400 | 48 | 1 |
| 4513 | 40 | 1 |
| 4321 | 49 | 1 |

TABLE H-continued

Summary of Biological Activity Screen for Platelet Aggregation

| TR No. | Example No. | Activity Value Platelet Aggregation |
|---|---|---|
| 4323 | 51 | 1 |
| 4322 | 50 | 1 |
| 4324 | 52 | 1 |
| 4428 | 53 | — |
| 4298 | 35 | 1 |

I claim:
1. A compound of the formula,

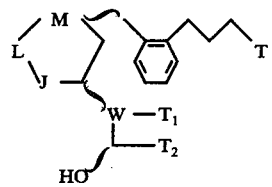

in which:
T is selected from the group consisting of carboxyl or alkoxycarbonyl;
M is carbonyl;
L is methylene;
J is ethylene;
W is

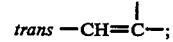

$T_1$ and $T_2$ are attached to adjacent carbon atoms;
$T_1$ is hydrogen only if $T_2$ is loweralkyl; and
$T_2$ is selected from the group consisting of loweralkyl having 1-5 carbon atoms or a polymethylene radical having 4-6 carbon atoms;
provided, however, that $T_2$ is the polymethylene radical only when it is joined with W to form a cycloalkylidene radical having 6-8 carbon atoms.

2. A compound according to claim 1, methyl 4-2'-{[2S-(3S-hydroxy-1EE-octenyl)-6-oxocyclohex-1S-yl]methyl}phenylbutanoate.

3. A compound according to claim 1, methyl 4-2'-{[2R(3S-hydroxy-1E-octenyl)-6-oxocyclohex-1R-yl]methyl}phenylbutanoate.

4. A compound according to claim 1, methyl 4-2'-{[2S-(2S-hydroxy-E-cyclohexylidenemethyl)-6-oxocyclohex-1S-yl]methyl}phenylbutanoate.

5. A compound according to claim 1, methyl 4-2'-{[2R-(2S-hydroxy-E-cyclohexylidenemethyl)-6-oxocyclohex-1R-yl]methyl}phenylbutanoate.

* * * * *